United States Patent [19]

Pumphrey et al.

[11] Patent Number: 5,001,417

[45] Date of Patent: Mar. 19, 1991

[54] APPARATUS FOR MEASURING ELECTROLYTES UTILIZING OPTICAL SIGNALS RELATED TO THE CONCENTRATION OF THE ELECTROLYTES

[75] Inventors: John G. Pumphrey, Eden Prairie, Minn.; Benton A. Durley, III, Antioch, Ill.; Paul E. Garrett, Greenville, Ohio; Edward G. Pumphrey, Colorado Springs, Colo.; Charles L. Davis, Flower Mound, Tex.; Frederic L. Clark, Plano, Tex.; Lawrence Spritzer, Flower Mound, Tex.

[73] Assignee: Abbott Laboratories, Abbott Park, Ill.

[21] Appl. No.: 196,120

[22] Filed: May 25, 1988

Related U.S. Application Data

[63] Continuation-in-part of Ser. No. 56,605, Jun. 1, 1987, abandoned.

[51] Int. Cl.$^5$ ............... G01N 27/414; G01N 27/417; G01N 21/01
[52] U.S. Cl. .................. 324/71.5; 324/71.1; 324/425; 422/64; 422/72; 422/102; 204/406; 204/412; 204/416
[58] Field of Search ............ 324/71.1, 71.5, 425, 324/438, 96, 71.2; 422/64, 72, 102, 68; 357/25; 350/342; 204/406, 412, 416; 455/617

[56] References Cited

U.S. PATENT DOCUMENTS

| | | | |
|---|---|---|---|
| 4,018,509 | 4/1977 | Boswell et al. | 350/342 |
| 4,020,830 | 5/1977 | Johnson et al. | 357/25 X |
| 4,298,839 | 11/1981 | Johnston | 324/96 X |
| 4,330,870 | 5/1982 | Arends | 455/617 |
| 4,368,480 | 1/1983 | Senturia | 357/25 |
| 4,502,937 | 3/1985 | Yagi | 204/406 |
| 4,517,160 | 5/1985 | Galle et al. | |
| 4,564,422 | 1/1986 | Simoneau | 324/71.2 X |
| 4,654,127 | 3/1987 | Baker et al. | 204/406 X |
| 4,695,430 | 9/1987 | Coville et al. | 422/102 X |

OTHER PUBLICATIONS

Introducing Vision—Whole Blood Analysis, published by Abbott Laboratories, 12-1985.
Two-Dimensional Centrifugation for Desk-Top Clinical Chemistry, reprinted from Clinical Chemistry, Sep. 1985, by Steven G. Schultz, James T. Holen, Joseph P. Donohue and Therese A. Francoeur.

Primary Examiner—Kenneth Wieder
Assistant Examiner—Jack B. Harvey
Attorney, Agent, or Firm—John W. Cornell; Daniel W. Collins; Richard D. Schmidt

[57] ABSTRACT

Apparatus for measuring electrolyute concentrations in fluid samples. The apparatus includes an ion selective electrode having a plurality of ion selective detection sites. Each site has an affinity for a preselected electrolyte of interest and generates a potential having a magnitude related to the concentration of the corresponding electrolyte in the sample. A voltage to optical transducer circuit is provided to convert the voltage differentials to optical signals having intensity related to the concentration of the electrolytes in a first embodiment, a digital code related to the concentration of the electrolytes in a second embodiment, and an optical absorption or density value related to the concentration of the electrolytes in a third embodiment. The optical signals are suitable for detection by conventional optical detector apparatus of assay instruments and may be processed using conventional two point linear interpolation techniques to determine the concentrations of the preselected electrolytes.

69 Claims, 11 Drawing Sheets

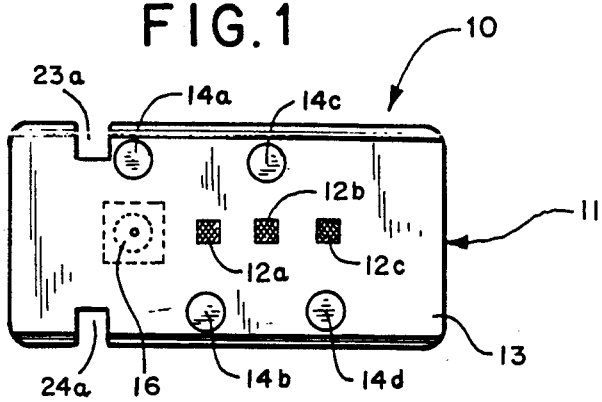
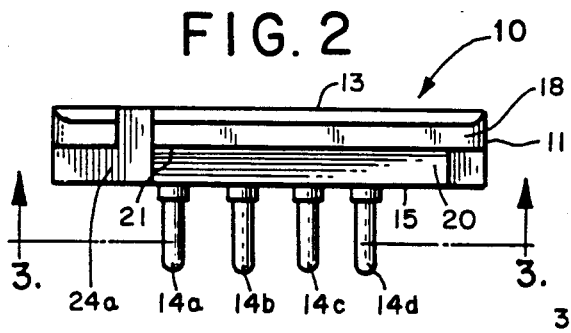
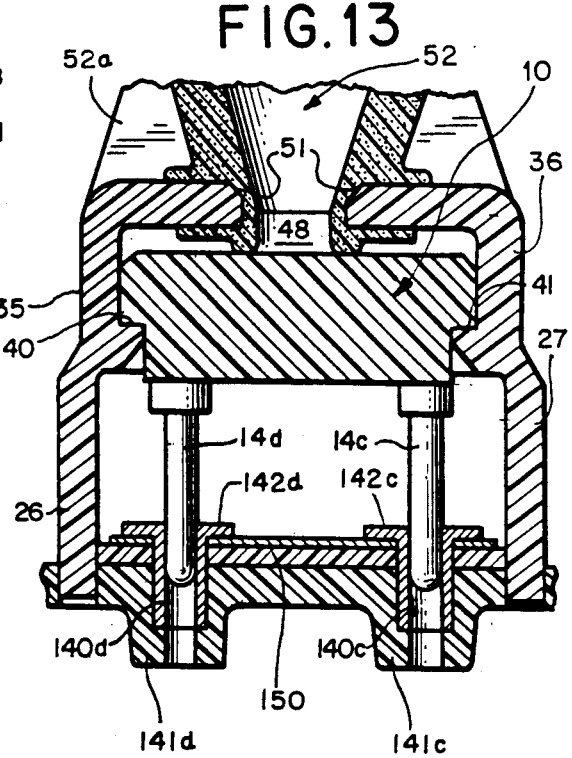
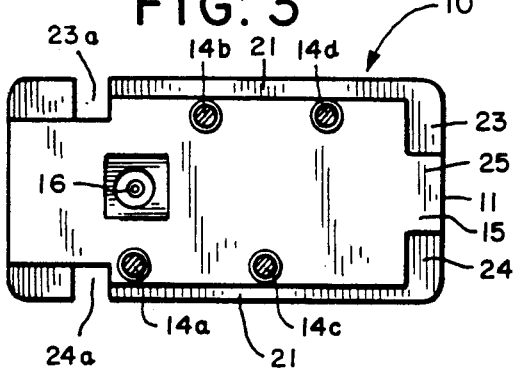
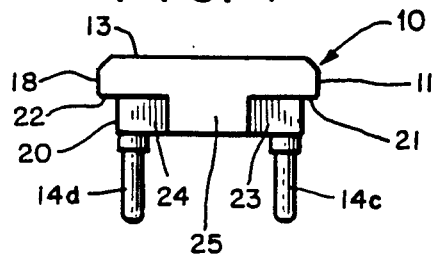

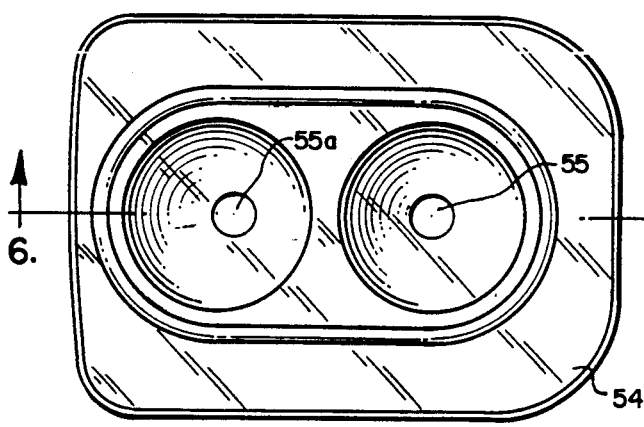
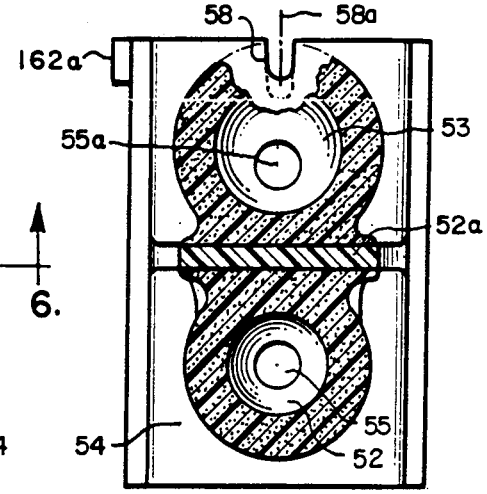
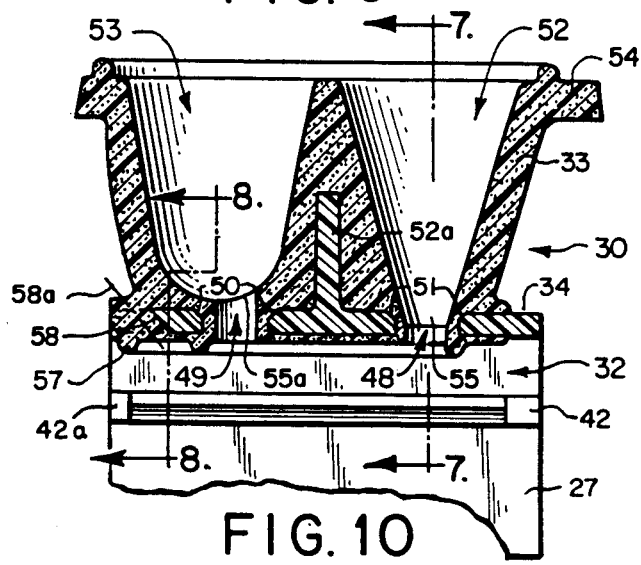
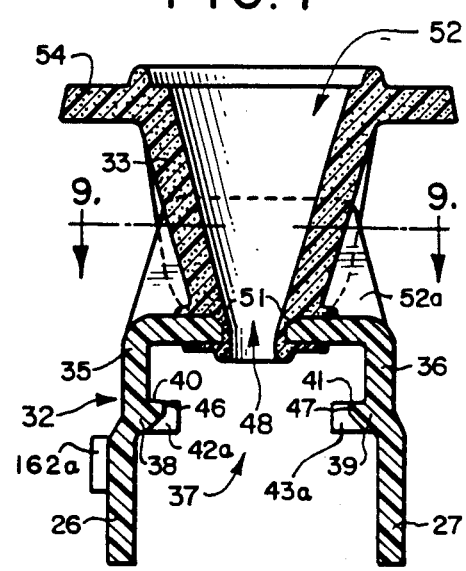
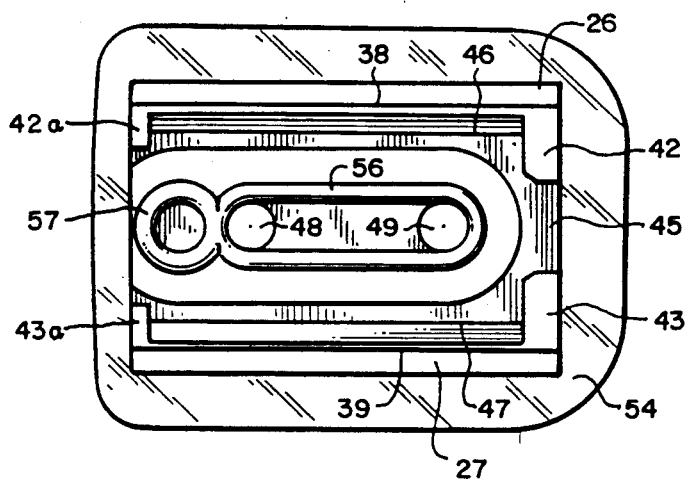
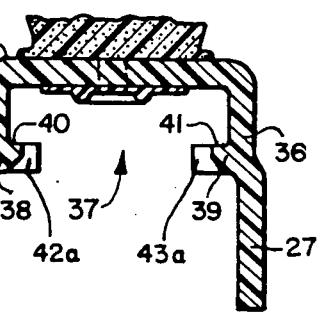

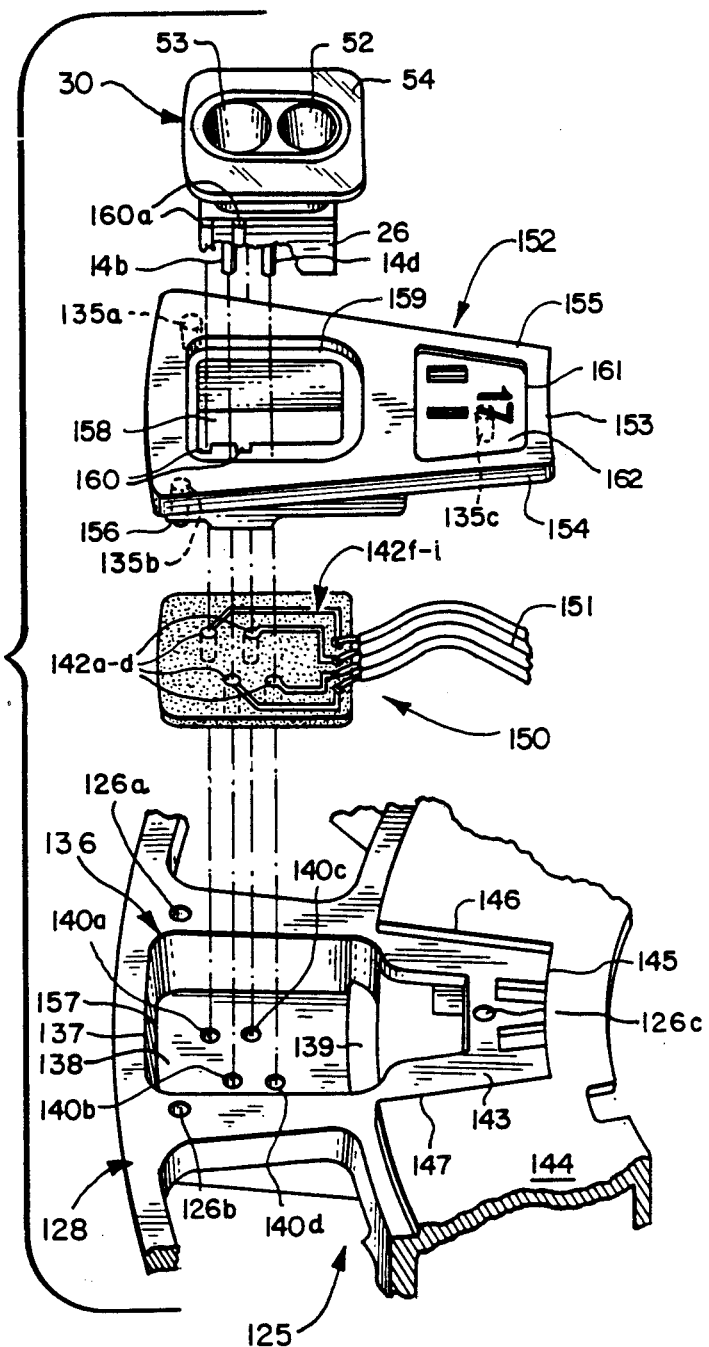
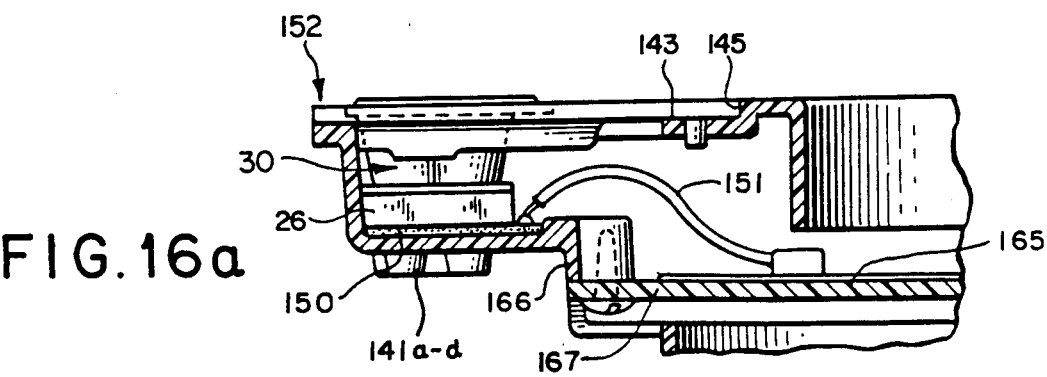

APPARATUS FOR MEASURING ELECTROLYTES UTILIZING OPTICAL SIGNALS RELATED TO THE CONCENTRATION OF THE ELECTROLYTES

STATEMENT OF RELATED APPLICATION

This application is a continuation in part of U.S. application Ser. No. 056,605 filed June 1, 1987 now abandoned.

BACKGROUND OF THE INVENTION

1. Field Of The Invention

This invention relates generally to apparatus for measuring the concentrations of electrolyte components such as sodium, potassium, and others in fluid samples, such as biological fluids. More particularly, the invention relates to apparatus for electrically measuring the concentrations of selected electrolytes in such samples and for generating optical signals representative of the measured concentrations of the selected electrolytes. Apparatus embodying the present invention is particularly advantageous for use in conjunction with existing automated assay instruments which employ optical sources and detectors to read assays and optically encoded data.

2. Description Of Related Art

It is often necessary or desirable in determining and evaluating the condition of a patient to determine the concentration of certain electrolytes in the patient's system. Typically, the presence and concentration of electrolytes is determined by analyzing a sample of whole blood or blood serum taken from the patient. Common electrolyte components of interest include potassium, sodium, chloride, carbon dioxide, lithium, ammonium, and pH, to name a few.

Traditionally, such electrolytes have been detected and measured using flame spectrophotometric techniques. Generally, in flame spectrophotometry, a chemical composition is prepared from a sample containing the electrolyte or electrolytes of interest. The composition is then combusted and optical measurements of the resulting flame are made. The spectral characteristics of the flame are then analyzed to determine the presence and concentration of the electrolytes of interest in the sample The value of flame spectrophotometric techniques is limited by their ability to operate on serum only and not whole blood. In addition, in flame spectrophotometry, it is critical but very difficult to precisely control the combustion of the prepared compound. Consequently, with this technique it is typically not possible to obtain a high degree of accuracy and repeatability, both of which are highly desirable characteristics.

In order to overcome the drawbacks and limitations associated with traditional flame spectrophotometric techniques, ion selective electrode apparatus and measuring techniques have been developed. An ion selective electrode typically includes a specially formulated chemical membrane connected to one of a pair of electrodes. The other electrode typically serves as a reference. The membrane is specially formulated to have an affinity for a selected electrolyte of interest. When the membrane is exposed to a fluid sample containing the selected electrolyte of interest, it attracts the electrolyte and builds up an ionic charge which results in a measurable voltage differential between the two electrodes. The electrodes may be connected to electrical circuitry which converts the voltage differential into an electrical signal representative of the concentration of the selected electrolyte. Ion selective electrodes having an affinity for most if not all of the commonly known electrolytes have been developed. Ion selective electrodes have the ability to measure electrolyte concentrations directly from whole blood samples without the requirement of first filtering the blood sample to obtain serum. In addition, ion selective electrode technology provides highly sensitive, accurate, and repeatable electrolyte measurements.

Similarly to ion selective electrodes, chemical field effect transistors (Chem FET's) have also been developed and have been successfully employed in measuring electrolytes in fluid biological samples. Like ion selective electrodes, Chem FET's employ specially formulated chemical membranes having affinities for particular electrolytes of interest. However, unlike ion selective electrodes, which are completely passive devices, Chem FET's include a field effect transistor (FET) which is controlled by the ion charge on a membrane to allow current flow between the source and drain of the FET. This current flow is measurable and can be related to the concentration of the electrolyte of interest in the sample. Alternatively, Chem FET's have been utilized in a voltage mode by feeding back the drain-source current to vary the gate voltage and maintain the drain-source current constant. In this mode, the gate voltage varies measurably with electrolyte concentration Like ion selective electrodes, Chem FET's typically provide more accurate electrolyte measurements than traditional flame spectrophotometric techniques.

It is advantageous to include ion selective electrode or similar Chem FET technology in existing automated assay instruments in order to extend the range of assays which such instruments can perform to include electrolytes. However, such instruments have typically been designed to measure assays optically and are therefore fundamentally incompatible with ion selective electrode and related Chem FET technology which is based upon electrical measurement of assays. Thus, in the past in order to incorporate the two technologies, it has typically been necessary to extensively modify existing instruments by the addition of special electronics in order to take advantage of ion selective electrode or Chem FET technology. Attendant with the requirement of such modifications have been increased cost, inconvenience, and sometimes unreliability.

The present invention seeks to overcome the foregoing drawbacks and limitations of the prior art by providing apparatus for measuring electrolyte concentrations in biological samples which takes advantage of preferred ion selective electrode technology and techniques and which at the same time is compatible with existing automated assay instruments of the type utilizing conventional optical reader technology. It is a significant feature of the invention that the apparatus requires little if any modification of existing automated assay instruments on which it is to be used. Advantageously, the apparatus provides the flexibility, sensitivity, accuracy, and repeatability associated with ion selective electrode technology. At the same time, the apparatus reduces costs by providing the ability to utilize the optical assay reading or optical code reading apparatus present in existing automated assay instruments without modification. Another significant feature of the invention is the relatively low cost at which the apparatus can be manufactured and used. Still other advantages and features of the invention will become apparent from the detailed description of the presently preferred embodiments thereof which is set forth below.

SUMMARY OF THE INVENTION

The foregoing features and advantages of the invention are achieved by providing an apparatus for measuring electrolytes in a fluid sample comprising a sensor which is operative when brought into fluid contact with the sample to generate an electrical signal having a parameter related to the concentration of a preselected electrolyte in the sample. The apparatus further comprises a transducer circuit in communication with the sensor for generating a second signal having a parameter or value related to the value of the parameter of the electrical signal. The apparatus still further comprises an optical device which is responsive to the second signal to generate a corresponding optical signal which represents the concentration of the preselected electrolyte in the sample and which can be read by an assay instrument using existing optical reader apparatus.

BRIEF DESCRIPTION OF THE DRAWINGS

The novel features that are believed to be characteristic of the invention are set forth in the appended claims. The invention itself, together with the foregoing features and attendant advantages thereof, will be best understood by reference to the following detailed description of the presently preferred embodiments thereof, taken in conjunction with the drawings, in which:

FIG. 1 is a top plan view of an ion selective electrode comprising a portion of a first preferred embodiment of the invention;

FIG. 2 is a side elevation view of the ion selective electrode illustrated in FIG. 1;

FIG. 3 is a bottom plan view of the preferred ion selective electrode illustrated in FIG. 2, taken along a line 3—3;

FIG. 4 is a right side elevation view of the ion selective electrode as illustrated in FIGS. 1-3;

FIG. 5 is a top plan view of a sample container means comprising a portion of a first preferred embodiment of the invention;

FIG. 6 is a side elevation view in section of the sample container means of FIG. 5 taken along a line 6—6 showing sample vessels and interface means;

FIG. 7 is an elevational view in section of the sample container means illustrated in FIG. 6 taken along a line 7—7;

FIG. 8 is a partial elevational view in section of the sample container means illustrated in FIG. 6 taken along a line 8—8.

FIG. 9 is a top sectional view of the sample container means illustrated in FIG. 7 taken along a line 9—9;

FIG. 10 is a bottom plan view of the sample container means including the sample vessels and interface means;

FIG. 13 is a sectional view of the interconnected ion selective electrode and sample container means illustrating the fluid-tight connection therebetween;

FIG. 16 is a partial exploded view in perspective of the sensor unit of a first preferred embodiment with an adaptor means, connector, and sample delivery carousel for use with an automated assay instrument;

FIG. 16a is a partial perspective view of the sensor unit, adaptor means, connector, and carousel illustrated in FIG. 16 showing the components mounted in the carousel;

DETAILED DESCRIPTION OF THE PRESENTLY PREFERRED EMBODIMENTS

Figure 11:
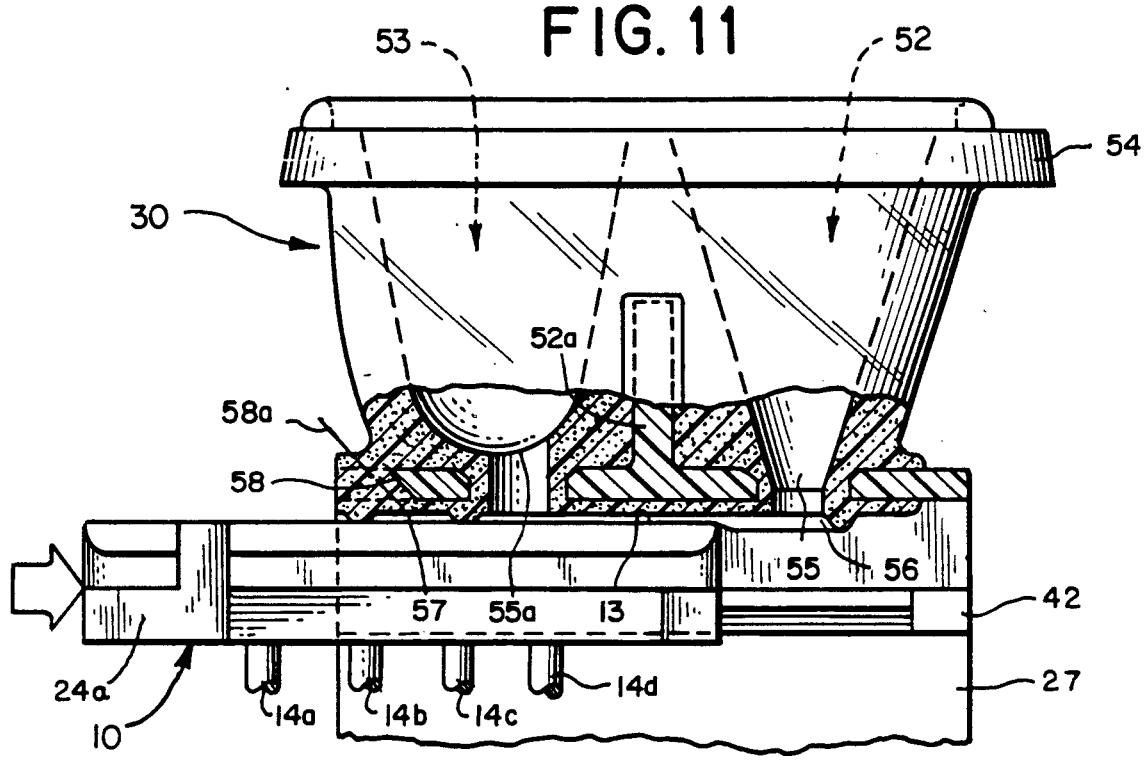
FIG. 11 is a side elevation view partially in section, illustrating a partial mechanical interconnection of the ion selective electrode and the sample container means of a first preferred embodiment.
Figure 12:
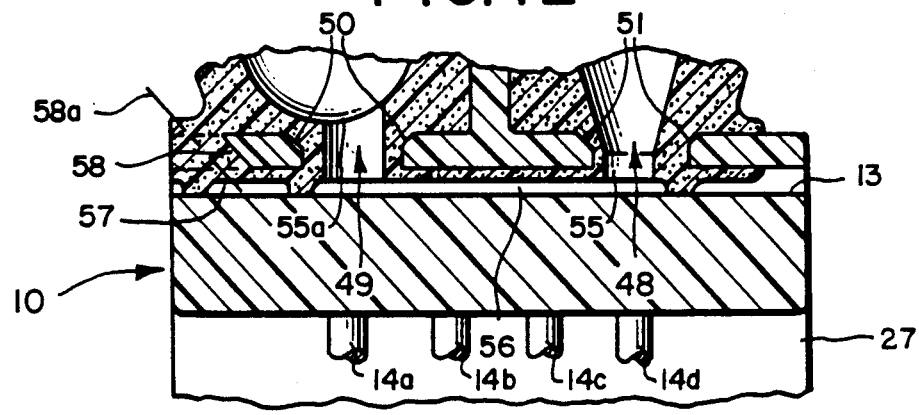
FIG. 12 is a partial side elevation view in section of the complete mechanical connection between the ion selective electrode and the sample container means of a first preferred embodiment.
Figure 14:
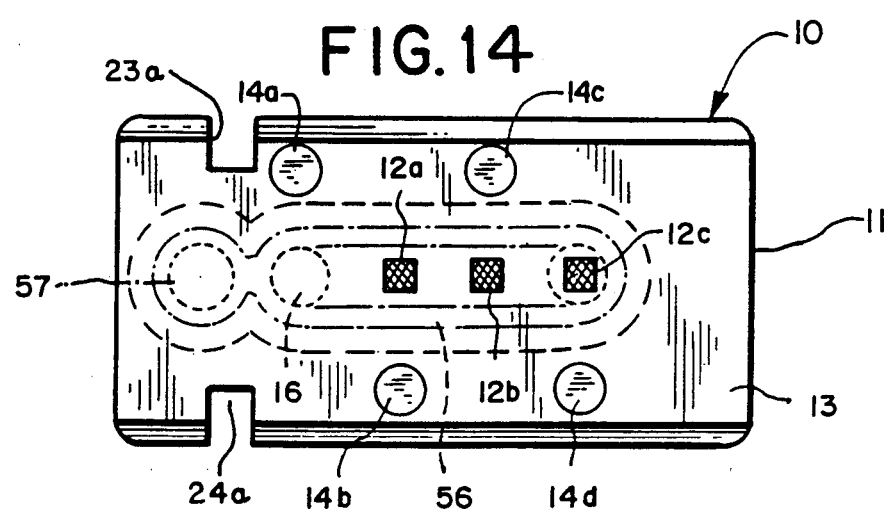
FIG. 14 is a top plan view of the ion selective electrode showing the positions of the ion selective detection sites and the reference electrode thereof relative to the position of the fluid tight gasket of the sample container means, which is superimposed thereon.

In broad terms, the preferred embodiments of the invention comprise apparatus which is operative to electrically measure the concentrations of selected electrolytes in a biological sample and to generate optical signals representing the measured concentrations which are readable by conventional optical detector equipment. A first preferred embodiment is advantageously employed in conjunction with existing automated assay instruments of the type utilizing sample delivery carousels and conventional optical detector apparatus such as photo-multiplier tubes (PMT's) for reading assays. A second preferred embodiment is advantageously employed in conjunction with such instruments having conventional optical detector apparatus for reading optically encoded data such as bar codes. Exemplary applications of the first and second preferred embodiments to a typical automated assay instrument of the type identified is described in detail below.

A third preferred embodiment is advantageously employed in conjunction with known automated centrifugal assay instruments of the type utilizing multichamber test cartridges and conventional optical source and detector apparatus such as PMT's. An exemplary application of the third preferred embodiment to a typical instrument of this type is also described in detail below.

It is understood, however, that the broad principles of the invention are not limited by the particularly advantageous applications of the preferred embodiments. Rather, the broad principles of the invention are applicable to other types of existing automated instruments, to stand-alone, non-automated applications with optical reading apparatus, and to many other applications where it is necessary or desirable to measure assays electrically and to read the measurements optically. It is also understood that application of this invention is not limited to use with biological fluids but is also applicable to any fluid in which it is desirable to measure electrolytic components.

With this in mind, and referring to FIGS. 1–4 and 15, a first preferred embodiment generally comprises electrode means which when brought into fluid contact with a fluid sample, are operative to generate a plurality of voltage potentials having magnitude related to the concentrations of a corresponding plurality of selected electrolytes in the sample; transducer circuit means operative to convert the voltage potentials into electrical signals each having a parameter, such as duty cycle, related to the magnitude of the corresponding voltage potential; and, optical output means, which is driven by the electrical signals to generate optical output signals representing the concentrations of the selected electrolytes in the sample which are readable by conventional optical detector apparatus.

The electrode means preferably comprises a multichannel ion selective electrode 10. The ion selective electrode 10 preferably comprises a planar substrate 11 having a selected plurality of ion selective detection sites 12a, 12b, and 12c, formed on a first surface 13 thereof and a plurality of electrically conductive pins 14a, 14b, 14c, and 14d, extending from a second opposite surface 15 thereof. Each detection site 12a–c includes a selected ion-selective membrane (not shown). In addition, the substrate 11 preferably has formed on the first surface 13 thereof, a reference electrode 16. One of the electrically conductive pins 14a is conductively connected to the reference electrode 16. Each of the remaining pins 14b–14d is conductively connected to one of the ion selective detection sites 12a–c. The locations of the conductive pins 14a–14d relative to the reference electrode 16 and the detection sites 12a–12c is not critical and is dictated primarily by convenience. However it is preferred that the reference electrode 16 and the detection sites 12a–c be aligned along the longitudinal center line of the substrate 11 for reasons which will become apparent. Although the preferred ion selective electrode 10 includes three ion selective detection sites 12a, 12b, and 12c, it is understood that fewer or more sites and corresponding conductive pins could be provided depending upon the application and size constraints.

The ion selective electrode is preferably constructed as taught in the co-pending application of J. Geist, S. Messner, and T. Schapira, Ser. No. 053 446 filed on May 22, 1987 and entitled Ion-Selective Electrode Having A Non-Metal Sensing Element, which is commonly assigned with this application. The disclosure of the co-pending application is incorporated herein by reference. In addition, the ion selective membranes at the detection sites 12a–c are suitably formulated of known ion-selective chemical compositions, such as those disclosed in the co-pending application. It is understood that the exact formulations and combinations of formulations of the ion selective membranes are dependent upon the particular electrolytes which it is desired to measure. Many suitable formulations are known to those skilled in the art and need not be set out here.

The substrate 11 is preferably formed such that an upper portion 18 thereof is somewhat wider than and overhangs a lower portion 20 thereof to form mounting shoulders 21 and 22 on opposite longitudinal sides. In addition, at one longitudinal end of the substrate 11 notches 23 and 24 are preferably formed to provide an alignment tab 25, the function of which is described in detail below. At the opposite longitudinal end, L-shaped notches 23a and 24a are preferably formed. The function of these notches is also described in detail below.

In connection with the advantageous application of the first preferred embodiment to carousel-containing automated assay instruments, the first preferred embodiment may also be provided with sample container means into which and from which samples to be measured can be introduced and removed, and which in use may be maintained in fluid-tight communication with the electrode means. Referring to FIGS. 5 through 10, the sample container means of the first preferred embodiment is preferably provided by sensor cup means 30 which comprises electrode interface means 32 and vessel means 33. The interface means 32 is preferably formed of a relatively stiff plastic such as an ABS, SAN, or polysulfone plastic by conventional plastic molding techniques. The preferred interface means 32 has an elongated flat top surface 34 integrally formed with opposite side surfaces 35 and 36. The longitudinal dimensions of the top surface 34 and side surfaces 35 and 36 are preferably equal to the longitudinal dimension of the ion selective electrode 10. The top surface 34 and side surfaces 35 and 36 together form a mounting slot 37 preferably having an interior width dimension which corresponds to the outside width dimension of the ion selective electrode 10 and which is adapted to receive and hold the ion selective electrode 10. The side surfaces 35 and 36 each have underturned lips 38 and 39 which form longitudinal mounting shoulders 40 and 41 corresponding to the mounting shoulders 21 and 22 of the substrate 11 of the ion selective electrode 10 and which support the ion selective electrode 10 in the mounting slot 37.

Near one longitudinal end of the preferred interface means 32, horizontal projections 42 and 43 extend from the opposite underturned lips 38 and 39 into the mounting slot 37 to form an alignment or mounting notch 45 preferably having dimensions corresponding to the tab 25 formed on the substrate 11 described above. The mounting notch 45 ensures proper alignment and orientation of the ion selective electrode 10 by engaging the corresponding tab 25 of the substrate 11 when the ion selective electrode 10 is completely mounted in the mounting slot 37. The width dimension of the notch 45 is narrower than the width of the area between the L-shaped notches 23a and 24a of the electrode 10 and thus prevents mounting the electrode 10 in the interface means 32 with the wrong orientation. Near the opposite longitudinal end of the interface means 32, a second pair of horizontal projections 42a and 43a extend inwardly from the opposite underturned lips 38 and 39. These projections are dimensioned and positioned to engage and lock into vertical portions of the L-shaped notches 23a and 24a of the electrode 10 when the electrode 10 is mounted in the mounting slot 37 in a storage position, which is described in detail below. The projections 42a and 43a slide in the horizontal portions of the L-shaped notches 23a and 24a respectively when the electrode 10 is pushed from the storage position to an operational position. The underturned lips 38 and 39 are provided with longitudinal substrate contact surfaces 46 and 47 and are dimensioned so that these surfaces fit flush against the opposite side surfaces of the lower portion 20 of the substrate 11 when the electrode 10 is positioned in the mounting slot 37. The contact between the surfaces 46 and 47 and the surfaces of the substrate 11 provide a friction fit which assists in holding the ion selective electrode 10 in proper position in the mounting slot 37.

A pair of cylindrical openings 48 and 49 having frustoconical tops 50 and 51 respectively are formed in longitudinal alignment in the top surface 34 of the interface means 32. The openings 48 and 49 are positioned in the top surface 34 so that when the ion selective electrode 10 is completely mounted in the mounting slot 37, the openings 48 and 49 are centered immediately above the reference electrode 16 and the outside detection site 12c respectively on the first surface 13 of the ion selective electrode 10. A dividing wall 52a is preferably formed integrally with and perpendicular to the top surface 34 between the openings 48 and 49 to provide isolation and support therebetween and means for aligning the vessel means 33 and interface means 32.

The vessel means 33 is preferably formed as an integral unit of a relatively soft plastic by conventional plastic molding techniques. The vessel means 33 is preferably molded around the interface means 32 to form a composite part prior to the ion selective electrode 10 being mounted in the mounting slot 37 of the interface means 32. The vessel means 33 comprises a pair of fluid vessels 52 and 53 and a connecting horizontal shelf 54. Each vessel 52, 53 has a bottom opening 55, 55a which is aligned concentrically with the corresponding opening 48, 49 in the top surface 34 of the interface means 32. The vessel means 33 is preferably molded so that a portion of the side walls of the fluid vessels 52 and 53 extends through the openings 48 and 49 in the top surface 34 of the interface means 32 to anchor the vessel means 33 to the interface means 32 to form a single composite unit and to facilitate fluid-tight interconnection of the ion selective electrode 10 and the sensor cup means 30.

The plastic which extends below the openings 48 and 49 is preferably molded in the form of a substantially elliptical gasket 56 which extends around the openings 48 and 49, and the reference electrode 16 and detection sites 12a-c of the ion selective electrode 10 when the ion selective electrode 10 is completely mounted in the mounting slot 37. As best shown in FIGS. 11-14, the relative softness of the plastic from which the vessel means 33 is constructed provides a fluid-tight fit with the first surface 13 of the ion selective electrode 10. The elliptical gasket 56 thus forms a fluid-tight channel which extends over the entire line of ion selective detection sites 12a-c formed in the first surface 13 of the ion selective electrode 10 when in use.

In addition to the elliptical gasket 56, a substantially circular gasket 57 is formed and contacts the first surface 13 of the substrate 11 in a friction fit to assist in holding the ion selective electrode 10 in position when in use. During storage, and prior to initial use, the ion selective electrode 10 is preferably positioned in the mounting slot 37 in a storage position which corresponds to less than complete insertion of the electrode in the slot. In the storage position, the vessel means 33 is preferably positioned relative to the ion selective electrode 10 such that the circular gasket 57 forms a fluid-tight chamber with the first surface 13 of the substrate 11 around the reference electrode 16. Also in the storage position, the elliptical gasket 56 forms a chamber around the detection sites 12a-c. As best shown in FIGS. 8-10, in one preferred embodiment a slot 58 is formed in the interface means 32 to provide a fluid passage to the fluid-tight chamber formed by circular gasket 57 about the reference electrode 16 in the storage position. A syringe or other suitable means may be inserted in the slot 58 through the soft plastic of the vessel means 33 along a line 58a to introduce liquid into the fluid-tight chamber to keep the reference electrode 16 moist during shipment and storage. In a second preferred embodiment, the cavity formed between the first surface 13 of the ion selective electrode and the surface of the vessel means 33 by the gasket 57 is enlarged. In this embodiment the vessel means 33 may be inverted and a dropper may be used to drop fluid into the cavity. The ion selective electrode may then be placed in the storage position while maintaining the entire assembly in an inverted position In this embodiment, a greater volume of fluid can be provided about the reference electrode to further ensure moistness.

In order to protect the conductive pins 14a-d against damage when the ion selective electrode 10 is mounted in the slot 37, a pair of skirts 26 and 27 are preferably integrally formed with the interface means 32 on opposite sides of the pins 14a-d. The skirts 26 and 27 extend downwardly from the bottoms of the respective side walls 35 and 36 preferably below the pins 14a-d In addition, the skirts 26 and 27 preferably extend along the entire longitudinal dimension of the interface means 32.

When the ion selective electrode 10 is mounted in the mounting slot 37 of the interface means 32, the electrode 10, interface means 32, and vessel means 34 advantageously comprise a single sensor unit 60 which may be used to perform one or a plurality of electrolyte measurements and be subsequently disposed of as a unit. Alternatively, the ion selective electrode 10 portion of the sensor unit 60 may be separated from the interface means 32 and retained for further use while the sensor cup means 30 is disposed of as a separate unit.

Figures 15, 15A:
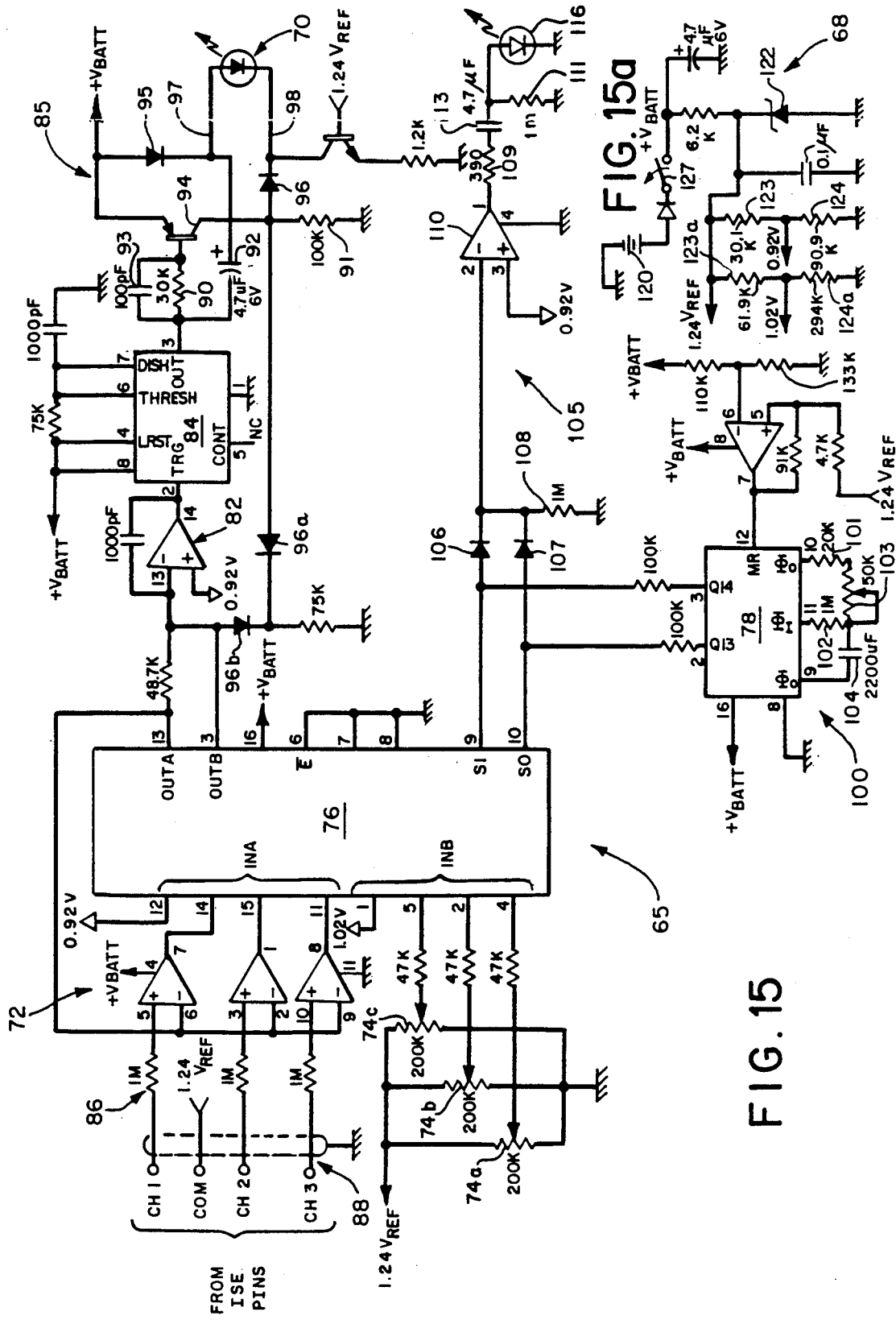
FIGS. 15 and 15a are electrical schematic diagrams illustrating the details of an optical output means and transducer circuit for converting voltage potentials on the ion selective electrodes to optical output signals comprising a portion of a first preferred embodiment.

Referring to FIGS. 15 and 15a, the details of the transducer circuit means 65 and the optical output means 70 of the first preferred embodiment are illustrated. The preferred transducer circuit means 65 generally includes DC power supply means 68, input buffer means 72, offset adjust means 74, analog switch means 76, and sample rate counter means 78. In addition, the preferred circuit includes integrator means 82 and pulse circuit means 84 which together function as voltage to duty cycle converter means, optical driver circuit means 85, and synchronization circuit means 105.

The conductive pins 14a-d of the ion selective electrode 10 are connected to inputs of the input buffer means 72 through 1 Mohm resistors 86 by a plurality of grounded shield conductors 88. The reference electrode 16 of the ion selective electrode 10 is also connected by a grounded shield conductor 88 to a DC reference voltage, which in the first preferred embodiment is approximately 1.24 volts, and which is generated by the power supply means 68 as described below.

The outputs of the input buffer means 72 are connected to a first set of inputs (IN A) of the analog switch means 76 which is preferably a dual four channel analog multiplexer (MUX) such as a CMOS MUX Part No. HC4052 or equivalent. The second set of inputs (IN B) of the analog switch means 76 is connected to outputs of the offset adjustment means 74 which comprises a three-channel variable voltage divider connected between the 1.24 volt DC reference and ground. The offset adjustment means 74 provides a variable offset voltage for each ion selective electrode input which is switched into the circuit together with the voltage differential of the corresponding input by the analog switch means 76 as described in detail below.

The outputs (OUT A, OUT B) of the analog switch means 76 corresponding to the first and second sets of inputs are connected in parallel to the inverting terminal of the integrator means 82. The non-inverting terminal of the integrator means 82 is connected to a 0.92 V DC reference which is generated by the power supply means 68 as described in detail below. The integrator means 82 and the input buffer means 72 preferably comprise operational amplifiers configured as illustrated. The three operational amplifiers comprising the input buffer means 72 and the operational amplifier comprising the integrator means 82 are suitably provided by a single CMOS Quad Operational Amplifier integrated circuit part no. TLC25L4C or equivalent.

The output of the integrator means 82 is connected to the trigger terminal (TRG) of the pulse circuit means 84, which is preferably a conventional monostable multivibrator circuit and which is suitably provided by a MOS timer such as part no. TLC555C or an equivalent. The pulse circuit means 84 is configured as illustrated to provide an output pulse having a high time of approximately 50 microseconds each time it is triggered by a negative-going signal from the output of the integrator means 82 as described in detail below.

The output of the pulse circuit means 84 is connected to the input of the optical driver circuit means 85. In the preferred embodiment, the optical driver circuit means 85 comprises a voltage doubler consisting of resistors 90 and 91, capacitors 92 and 93, PNP transistor 94, and diodes 95 and 96, configured as illustrated. The signal generated at the output terminals 97 and 98 of the optical driver circuit means 85 has approximately double the potential of the signal output by the pulse circuit means 84.

In the preferred embodiment, the optical output means 70 preferably comprises a green light emitting diode (LED) having an output wavelength of approximately 565 nanometers (nm). The preferred output wavelength corresponds to the emission wavelength which the existing optical detector apparatus of the Abbott TDx ® Analyzer is designed for. It is understood that other optical sources having different output wavelengths may be used as necessary to interface with different optical detector apparatus. The LED is connected across the output terminals 97 and 98 of the optical driver circuit means 85 with the anode of the LED being connected to terminal 97 and the cathode being connected to terminal 98. The voltage doubler circuit described above allows a wide variety of LED's having forward voltage drops up to approximately 2.2 volts to be used in the circuit with a minimum supply voltage of as little as 2.0 volts. It is understood that a non-doubling driver circuit could alternatively be used when it is not necessary to drive LED's having relatively large forward voltage drops with a low supply voltage.

The input select terminals S0 and S1 of the analog switch means 76 are connected to outputs Q13 and Q14 respectively of the sample rate counter means 78. The counter means 78 preferably comprises a 14-stage binary counter/oscillator such as an HC4060 CMOS counter or equivalent. The Q13 and Q14 outputs of the counter means 78 comprise the outputs of the 13th and 14th counter stages, which represent the count values $2^{13}$ and $2^{14}$ respectively. The counter means 78 is made to oscillate by the circuit 100 which is comprised of resistors 101 and 102, variable resistor 103, and capacitor 104 configured as illustrated. The circuit 100, when configured as illustrated, provides a count frequency of approximately 8 KHz which in turn provides a sample rate of approximately one sample per second, i.e., the combination of the Q13 and Q14 output states change every second to cause the analog switch means 76 to sequentially select each ion selective electrode pin 14b-d in turn. The sample rate can be adjusted as desired by varying the value of the variable resistor 103.

Also connected to the Q13 and Q14 outputs of the counter means 78 are inputs of a synchronization circuit means 105 which comprises diodes 106 and 107, resistors 108, 109, and 111, and comparator 110, capacitor 113, and LED 116, configured as illustrated. The diodes 106 and 107 are connected to the inverting terminal of the comparator 110 in an OR configuration. The noninverting terminal of the comparator 110 is connected to the 0.92 volt DC reference generated by the power supply means 68 and functions as an inverter. The output signal generated by the comparator 110 drives the LED 116 to cause it to illuminate at a predetermined intensity level set by the values of the resistors 109, 111 and capacitor 113 to provide an optical synchronization signal as described in detail below.

FIG. 15a illustrates the details of the power supply means 68. The power supply means 68 preferably includes a small, light source of DC voltage. In the preferred embodiment, a three cell nickel-cadmium battery 120 has been found suitable for use. The battery 120 generates a nominal supply voltage of approximately 4.3 V DC and supplies adequate current for operation of the preferred CMOS components of the transducer circuit means identified above. The power supply means 68 also preferably includes a precision voltage reference diode 122 connected between the positive and ground terminals of the battery 120 as illustrated to provide the 1.24 volt DC voltage reference utilized in the transducer circuit means 65 as described above The voltage reference 122 is preferably an LM 385 voltage reference or equivalent. A voltage divider comprising resistors 123 and 124 is preferably connected across the voltage reference 122 and provides a 1.02 volt DC reference at the junction of the resistors utilized in the transducer circuit 65 as the channel 1 input of the second set of inputs (IN B) to the analog switch means 76. A second voltage divider comprising resistors 123a and 124a is preferably connected across the voltage reference 122 in parallel to the first voltage divider and provides at the junction of the resistors the 0.92 volt DC reference which is utilized in the preferred transducer circuit 65 as described above.

In a particularly advantageous application of the first preferred embodiment of the electrolyte measuring apparatus, the apparatus interfaces with and is employed in conjunction with an existing automated assay instrument of the type having carousel-type sample delivery means and conventional optical reading means, such as a photomultiplier tube (PMT), photodiode, phototransistor means, or the like, for reading assays. A representative example of such instruments is the well-known TDx ® analyzer manufactured and sold by Abbott Laboratories of North Chicago, Illinois. The interfacing and utilization of the first preferred embodiment with the TDx ® analyzer will now be described it being understood that the TDx ® analyzer is merely illustrative and that the first preferred embodiment is also advantageously employed in conjunction with other automated assay instruments having the general characteristics identified above as well as with non-automated, stand-alone optical measuring apparatus.

Generally, the conventional "batch" carousel normally used with the TDx ® analyzer is adapted for use with the preferred electrolyte measuring apparatus by making several minor modifications, which are described in detail below, to accommodate the components of the preferred electrolyte measuring apparatus. However, no mechanical or electronic modifications to the instrument itself are required. Thus, the preferred apparatus provides an increased range of electrolyte tests not previously possible with the existing instrument with minimum cost and inconvenience.

Figure 16B:
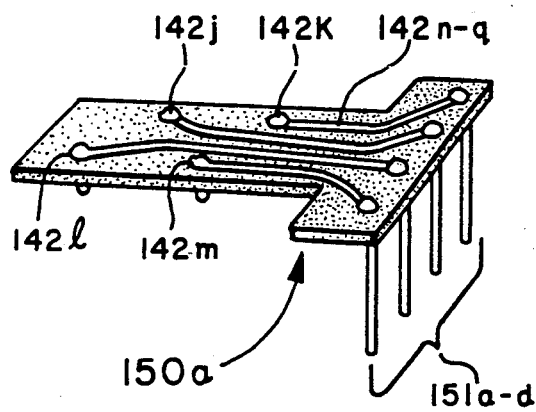
FIGS. 16b and 16c are partial perspective views illustrating respectively an alternative embodiment of the electrically conductive socket means 150 illustrated in FIG. 16 and of the LED 70 and spacer 170 illustrated in FIG. 18 for a second preferred embodiment of the invention.
Figure 16C:
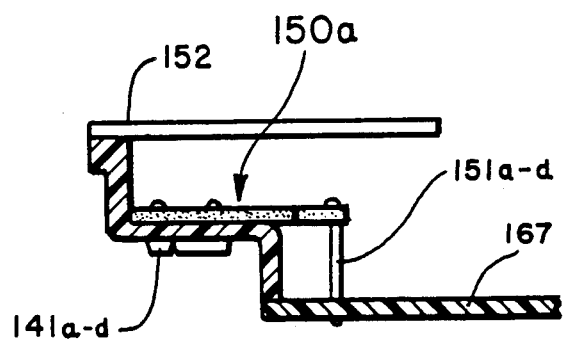
Figure 17A:
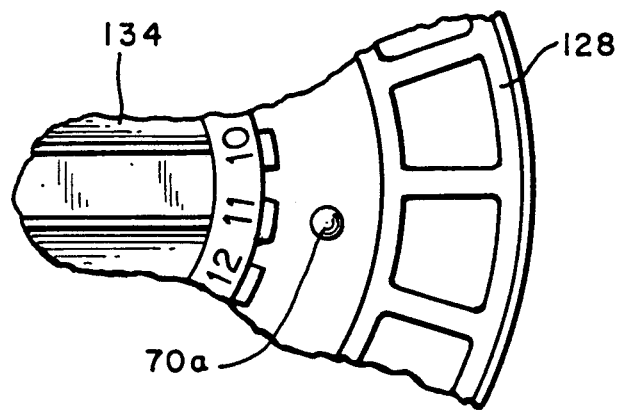
FIG. 17a is a partial top plan view of the sample delivery carousel of FIG. 17 illustrating an alternative placement of an LED 70a in a second preferred embodiment.
Figure 18A:
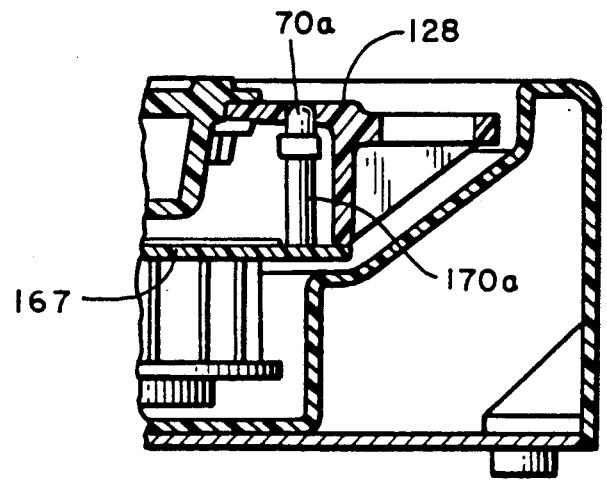
FIG. 18a is a partial side elevation view in section of the carousel and charging pack illustrated in FIG. 18 illustrating the adaptation of the carousel for use with a second preferred embodiment.
Figure 17:
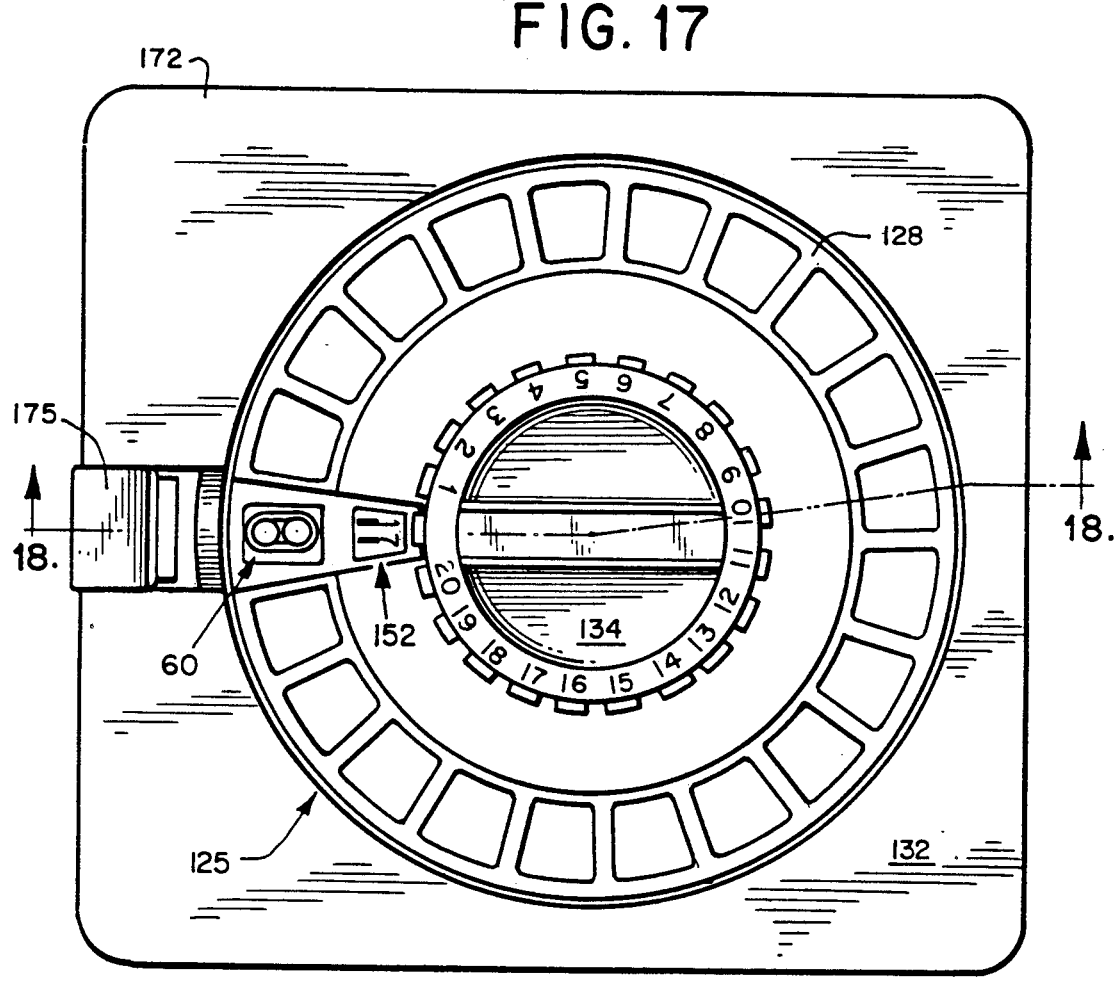
FIG. 17 is a top plan view of the sample delivery carousel adapted to contain the first preferred embodiment mounted in a charging pack.
Figure 18:
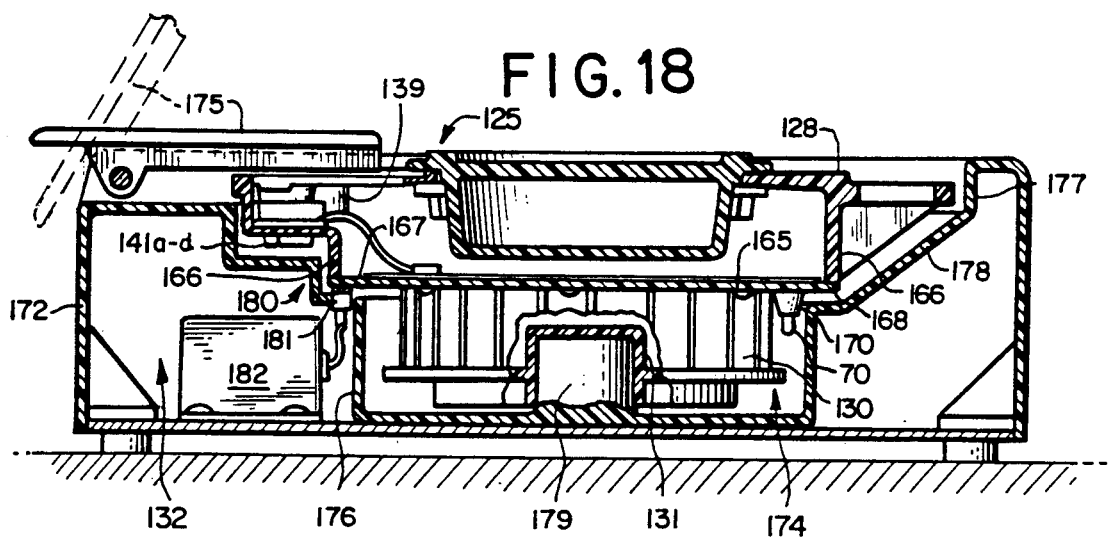
FIG. 18 is a side elevation view in section of the carousel and charging pack illustrated in FIG. 17 taken along a line 18—18, illustrating the adaptation of the carousel for use with a first preferred embodiment.

Referring to FIGS. 16-18, the conventional batch carousel 125 comprises an upper carousel section 128 which contains twenty-one positions, twenty of which are designed to hold sample containers, and a lower carousel section 130 connected thereto and containing a central spindle-receiving well 131 for mounting the carousel 125 in the instrument. In order to accommodate the first preferred embodiment of the electrolyte measuring apparatus, the upper carousel 128 is modified to locate an adaptor receiving well 136 in the twenty-first position The well 136 comprises an opening 137 formed in the top surface of the upper carousel section 128 and a chamber 138 which is enclosed on three sides and the bottom. The chamber 138 has an open side 139 which allows access into the center of the upper carousel section 128. Four small socket receiving openings 140a-d positioned corresponding to the positions of the conductive pins 14a-d of the ion selective electrode are formed in the bottom surface of the chamber 138. A cylindrical boss 141a-d extends from the bottom surface of the chamber 138 below each opening 140a-d. The bottom of each boss preferably has a small drainage opening as shown in FIG. 13.

In the upper carousel section 128 a wedge-shaped indented area 143 is formed in a raised section 144 of the top surface extending inwardly from the opening toward the center of the carousel 125. The indented area 143 is formed such that the inside wall 145 formed with the raised section has an arcuate shape and the two side walls 146 and 147 have a generally diverging dimension Also formed in the top surface of the upper carousel section are mounting openings 126a-c, the function of which is described in detail below.

An electrically conductive socket means 150, preferably in the form of a flexible printed wiring board has four electrically conductive sockets 142a-d arranged in positions corresponding to the openings 140a-d in the bottom surface of the chamber 138. The socket means 150 is mounted in the bottom of the chamber 138 with the sockets 142a-d positioned in the corresponding openings 140a-d and supported by the corresponding bosses 141a-d. Each socket preferably is open at the bottom to allow fluid drainage through the openings 140a-d and out of the carousel 125. Preferably, the bosses 141a-d prevent any electrically conductive portion of the sockets 142a-d from extending out the bottom of the chamber 138. Printed conductors 142f-142i on the flexible socket means 150 electrically connect the sockets 142a-d respectively with a multi-wire shielded connector 151. The connector 151 extends through the open side 139 of the chamber 138 into the center of the upper carousel section 128 and is connected to the transducer circuit means 65 described above, which is mounted in the carousel 125, preferably as described below.

Adaptor means 152 having a substantially wedged shape and dimensions corresponding to the dimensions of the opening 137 and the indented area 143 in the top surface of the upper carousel section 128, mounts in the opening 137 and chamber 138. The adaptor means 152 has an inner arcuate edge 153 which corresponds to and abuts the arcuate wall 145 formed by the indented area 143 when the adaptor means 152 is mounted on the carousel 125. Also, the adaptor means 152 has diverging lateral edges 154 and 155 which fit flush with the side walls 146 and 147 bordering the indented area 143 and a generally arcuate vertical retaining wall 156 which extends downwardly from the bottom surface of the adaptor means 152 in proximity to the outer periphery thereof and abuts the inside surface of the outer wall 157 of the chamber 138 so that when the adaptor means 152 is mounted in the opening 137 and chamber 138 it is securely held against motion both laterally and radially. In addition the adaptor means 152 preferably includes tapered pins 135a-c which are positioned corresponding to the position of the mounting openings 126a-c is the upper carousel section 128. The tapered pins preferably have a maximum diameter slightly greater than the diameter of the openings 126a-c so that when the adaptor means 152 is mounted in the chamber 138, the pins 135a-c and openings 126a-c join in a secure friction fit to hold the adaptor means 152 in place. Preferably, a permanent glue or other adhesive is applied to the pins 135a-c so that the adaptor means 152 is permanently mounted to the carousel 125.

An opening 158 having a shape and dimensions corresponding to the shapes and dimensions of the ion selective electrode 10 and the electrode interface means 32 described in detail above is formed in the adaptor means 152 for receiving and holding the sensor unit 60 comprised of the sensor cup means 30 and the ion selective electrode 10. An indented shelf 159 having shape corresponding to the shape of the shelf 54 of the sensor cup means 30 is formed around the opening 158 in the top surface of the adaptor means 152 to support the sensor unit 60 when it is mounted in the adaptor means 152. Key means are preferably provided in the adaptor means in the form of uniquely shaped and positioned notches 160 which are formed as part of the opening 158 and which are designed to receive correspondingly-shaped projections 160a on the interface means 32 of the sensor cup means 30. The key means is advantageously utilized to align the sensor unit 60 in the adaptor means 152 with the proper orientation and to associate selected adaptor means 152 and sensor units 60 to facilitate the identification and utilization of the proper sensor unit 60 for desired electrolyte measurements. Alternatively, additional projections and notches, or one or more other corresponding key structures could be provided for this purpose.

An indented area 161 is also formed in the top surface of the adaptor means 152 which may be advantageously used to receive and locate a coded label 162. The label 162 may be read by conventional optical reading apparatus such as a bar code reader and may be used to identify the particular electrolyte measurement or measurements which the sensor unit 60 mounted in the adaptor means 152 is designed to perform. Other information of interest may also be included.

When the sensor unit 60 is mounted in the adaptor means 152, the electrically conductive pins 14a-d of the ion selective electrode 10 extend downwardly through the open bottom of the adaptor means 152. When the adaptor means 152 is mounted in the opening 137 and chamber 138 of the carousel 125, these pins 14a-d are aligned with and mate with the corresponding sockets 142n-d mounted in the openings 140a-d in the bottom of the chamber 138. Electrical connection between the pins 14a-d and the preferred transducer circuit means 65 described in detail above is thereby obtained through the flexible printed connector 150 and shielded connector 151.

The preferred transducer circuit means 65 are mounted on a generally circular printed circuit board 165 which is preferably mounted horizontally between the upper carousel section 128 and the lower carousel section 130 in the center of the carousel 125. The printed circuit board 165 is preferably connected to anchors which are formed integrally with the inside surface of a circular wall 166 comprising a portion of the upper carousel section 128 by means of screws or other suitable fastening means before the upper and lower carousel sections 128 and 130 are connected. Preferably, the printed circuit board 165 has a fan-shaped section 167 which extends outwardly to a location adjacent to the bottom surface of the chamber 138 of the adaptor receiving well 136. This section preferably contains a pair of printed, electrically conductive contact areas (not shown) which are connected to the positive and negative terminals of the battery 120 described above for conducting charging current from the charging pack 132 to the battery 120. In addition, the printed circuit board 165 preferably has a small section 163 which extends outwardly between the upper and lower carousel sections 128 and 130 on the side of the carousel directly opposite the adaptor receiving well 136 for mounting the optical output means 70. In the first preferred embodiment, the LED which comprises the optical output means 70 is mounted on an insulating space; 170 which is in turn mounted to the printed circuit board 165. The spacer 170 is preferably dimensioned to align the LED with the optically sensitive portion of the optical reading apparatus of the automated instrument. In the exemplary case of the TDx ® analyzer, the spacer 170 is dimensioned to align the LED directly with the surface of the photomultiplier tube (PMT) of the reading apparatus. Similarly, the LED 116, which comprises the output of the synchronization circuit means 105, is preferably mounted on the circuit board 165 in alignment with optical detection apparatus and used to synchronize operation of the detection apparatus and transducer circuit means. In the case of the TDx ® analyzer, for example, the LED 116 is preferably aligned with the infrared optical detector used to detect the presence of cuvettes in the carousel 125.

It is desirable to minimize the necessity of disassembling the carousel 125 to replace the battery 120 of the power supply), means 68 mounted on the printed circuit board 165. A charging pack 132 is therefore advantageously provided for recharging the battery 120 between uses. The charging pack 132 preferably comprises a housing 172 having a carousel-receiving well 174 and a hinged sensor cover 175. The carousel-receiving well 174 includes a first vertical cylindrical wall 176 having an inside diameter corresponding to the outside diameter of the lower carousel section 130 and a second vertical cylindrical wall 177 concentric with the first wall 176 and at a higher elevation, having an inside diameter corresponding to the outside diameter of the upper carousel section 128. The first and second cylindrical walls 176 and 177 are connected by a frustoconical wall 178. In addition, a cylindrical mounting spindle 179 extends vertically from the floor of the carousel-receiving well 174 concentric with the first and second vertical walls 176 and 177. The mounting spindle 179 has an outside diameter which corresponds to the inside diameter of the spindle receiving well 131 of the lower carousel section 130 and which mounts the carousel 125 in the carousel-receiving well 174.

In one section of the connecting wall 178 adjacent to the sensor cover 175 a raised platform 180 is formed. A pair of parallel vertical retaining walls (not shown) are formed on top of the platform 175 with the distance between the retaining walls corresponding to the width of the chamber 138 of the upper carousel section 128. The platform 180 and retaining walls together form means which support and align the adaptor receiving well 136 of the carousel 125 when the carousel 125 is mounted in the charging pack 132.

A pair of electrically conductive spring contacts 181 are mounted on top of the first cylindrical wall 176 adjacent to and at opposite corners of the platform 180. These contacts 181 preferably comprise the output electrodes of a conventional charging circuit 182 which is mounted in the charging pack 132. When the carousel 125 is mounted in the charging pack 132, the flat contact areas on the underside of the printed circuit board 165 adjacent to the adaptor receiving well 136 of the carousel 125 contact these electrodes 181 and conduct charging current from the charging circuit 182 to the battery 120. In addition, a magnet (not shown) may be mounted in the charging pack 132 in alignment with a normally closed reed switch 127 of the power supply 68 to automatically open the switch 127 and remove supply voltage from the transducer circuit means 65 when the carousel 125 is mounted in the charging pack 132.

It is desirable when the sensor unit 60 is not in use that the ion selective membranes associated with the detection sites 12a-c of the ion selective electrode 10 be protected against contamination and evaporation. Accordingly, it is desirable to maintain a sufficient amount of a conventional buffer solution in the sensor cup means 30 to cover the membranes. The hinged sensor cover 175 may be advantageously rotated down to cover the sensor cup means 30 and prevent contamination of the membranes or evaporation of the buffer solution when the carousel 125 is mounted in the charging pack 132.

Operation of the first preferred embodiment of the electrolyte measuring apparatus will now be described. Generally, a small volume of the sample to be measured, which may be whole blood, serum, or plasma, is introduced into the fluid vessel 52 of the sensor cup means 30. The sample flows down through the bottom opening 55 of the vessel 52 and enters the fluid-tight channel formed by the elliptical gasket 56 of the vessel means 33 with the first surface 13 of the ion selective electrode 10. The sample flows over each of the detection sites 12a-c and over the reference electrode 16. Excess sample enters the fluid vessel 53 through the bottom opening 55a thereof. In order to obtain an accurate reading of the concentration of the selected electrolytes, a sufficient volume of sample must be introduced to completely cover each of the ion detection sites 12a-c and the reference electrode 16. In addition, for each sample to be measured, a sufficient volume is preferably introduced to completely purge old buffer solution, calibrator solution, or sample from the channel formed by the gasket 56. Other than these constraints, the actual volume of sample introduced into the sensor cup means 30 is not critical since the ion selective electrode 10 inherently generates voltage potentials on the conductive pins 14a-d connected to the corresponding detection sites 12a-c which are independent of sample volume. It is understood that the specific sensor cup means 30 described is advantageous for use with existing assay instruments of the previously described type. Other means for bringing samples into fluid contact with the detection sites and reference electrode may also be used depending upon the desired application of the electrolyte measuring apparatus.

In order to obtain an accurate and stable measurement, it is preferred that the sample be allowed to remain in contact with the detection sites 12a-c and the reference electrode 16 for a minimum of approximately 15 seconds. During this time, ions of the electrolytes selected for measurement in the sample are attracted to the specific ion selective membranes having an affinity for those electrolytes, thereby causing voltage differentials to be generated on the corresponding conductive pins 14b-d relative to the reference voltage on pin 14a due to the accumulation of ionic charges on the membranes. The input buffer means 72 of the transducer circuit means 65 provide high impedance isolation between the conductive pins and the transducer circuit means to prevent the flow of current through the ion selective membranes of the detection sites. The offset adjustment means 74 provides means for adjusting the response of the transducer circuit means 65 to accommodate ion selective electrodes 10 having a range of output signal levels while retaining linear response The variable resistors 74a-c of each channel of the offset adjustment means 74 are preferably adjusted so that the response of the transducer circuit means 65 remains linear over the expected signal level range of the ion selective electrode 10 for each channel. Alternatively, if the range of signal levels of a selected ion selective electrode 10 is known, the variable resistors 74a-c of the offset adjustment means 74 may be replaced with fixed resistor values.

The sample rate counter means 78 sequentially counts through four output state combinations from "00" to "11" synchronously rnd continuously at the rate of approximately one combination sample per second. The nominal time period of each state is thus known and advantageously defines an optical integration period during which the optical detection apparatus will integrate the optical signals generated by the optical output means 70 for each selected electrode pin. In the TDx ® analyzer, for example, the PMT inherently operates to integrate detected optical signals until discharged at the end of the integration period. With other optical detector devices such as photodiodes and phototransistors, integrating capacitors may be used in a manner well known to those skilled in the art to integrate the signals generated by the detector during each integration period.

Each time the counter output is "00", i.e., during state 1, a synchronization state is defined. During the synchronization state, the comparator 110 drives the LED 116 at a fixed level, thereby causing it to illuminate. The illumination of the LED 116 is detected by the infrared optical detector of the TDx ® described above which provides a synchronization signal to synchronize the TDx ® with the operation of the transducer circuit means 65.

Also, during state 1, the analog switch means 76 applies the 0.92 volt and 1.02 volt DC references to the inverting terminal of the integrator means 82 in parallel. The integrator means 82 output voltage ramps down at a predetermined rate and triggers the pulse circuit means 84 when the output voltage equals approximately one-third of the supply voltage. The pulse circuit means 81 generates a square wave pulse having a duration of approximately 50 microseconds. The magnitude of the pulse relative to ground is approximately doubled by the optical driver circuit means 85 and is applied to the output terminals 97 and 98 to drive the LED 70 which illuminates at a predetermined intensity level and thereby produces an optical signal which is detectable by the PMT of the TDx ® analyzer. Since the same fixed reference voltage is applied to the integrator means 82 during each state 1 integration period, the PMT integrates the same fixed number of optical pulses during this period each time it occurs. The total integrated intensity of the optical pulses occurring during the state 1 integration period is advantageously utilized as a gain reference for the PMT for the three subsequent integration periods, i.e. states 2-4.

As each conductive pin of the ion selective electrode 10 which is connected to an input of the analog switch means 76 is sequentially selected by the sample rate counter means 78, the voltage differentials thereon are integrated by the integrator means 82. The integrator means 82, together with the pulse circuit means 84 functions as a voltage to duty cycle converter means. Each pulse generated by the pulse circuit means 84 is inverted by the PNP transistor 94 which reverse biases the diode 96a and causes a diode 96b to conduct, thereby pulling current out of the inverting terminal of the integrator means 82 and causing the output voltage thereof to ramp up. When the pulse terminates, the output of the integrator means 82 again ramps down at a rate determined by the magnitude of the voltage on its inverting terminal until the pulse circuit means 84 is again triggered. The time between optical output pulses and thus the duty cycle of the optical signal and the number of optical pulses occurring during an integration period is linearly dependent on the magnitude of the voltage differential on the input terminals of the integrator means 82. Thus, the total integrated intensity of the optical output pulses occurring during an integration period is linearly related to and represents the concentration of the selected electrolyte corresponding to the selected electrode pin. It is understood that although in the preferred embodiment the duty cycle of the optical signal has been selected as the parameter representing the concentration of the selected electrolyte, other parameters such as frequency, pulse width, or magnitude of the optical signal could also be modulated by transducer circuit means and used to represent electrolyte concentration.

The concentration of the selected electrolyte may be determined from the total integrated intensity of the optical pulses by conventional linear interpolation techniques using e conventional two point calibration process Briefly, before measuring an unknown sample a first calibrator sample having known, relatively low concentrations of the electrolytes of interest is measured and the integrated intensity of the resulting optical signal is determined. Next, a second calibrator sample having known, relatively high concentrations of the electrolytes of interest is measured and the integrated intensity of the optical signal is determined. Since the response of the transducer circuit means 65 is linear, the integrated intensity of the optical signal measured for the actual sample can be linearly interpolated to determine the concentration of the electrolytes in the sample from the integrated intensities and known concentrations corresponding to the calibrator samples.

Figure 19:
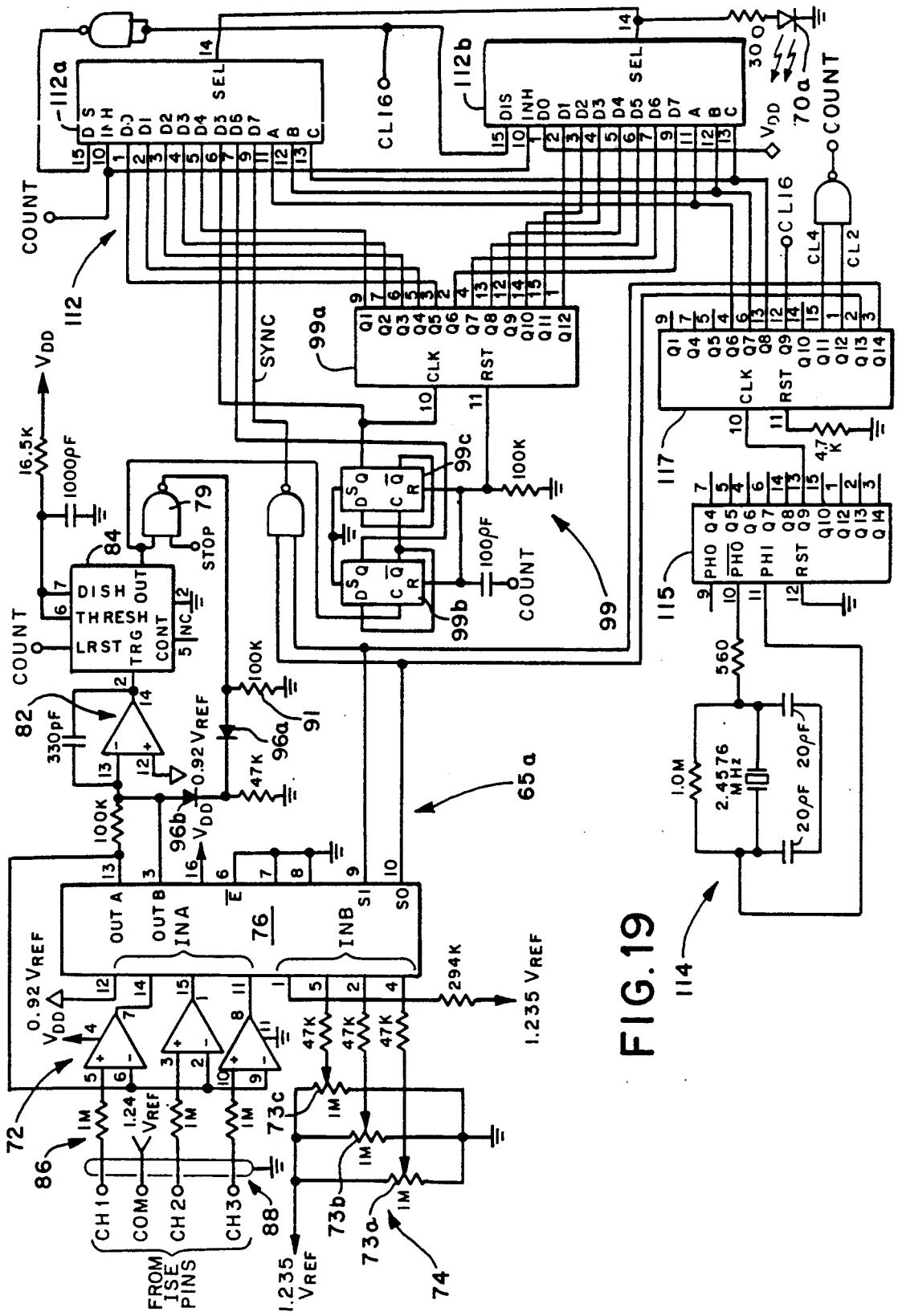
FIGS. 19 and 19a are electrical schematic diagrams illustrating the details of an alternative optical output means and transducer circuit for converting voltage potentials on the ion selective electrodes to optical output signals comprising a portion of a second preferred embodiment of the electrolyte measuring apparatus of the invention.
Figure 19A:
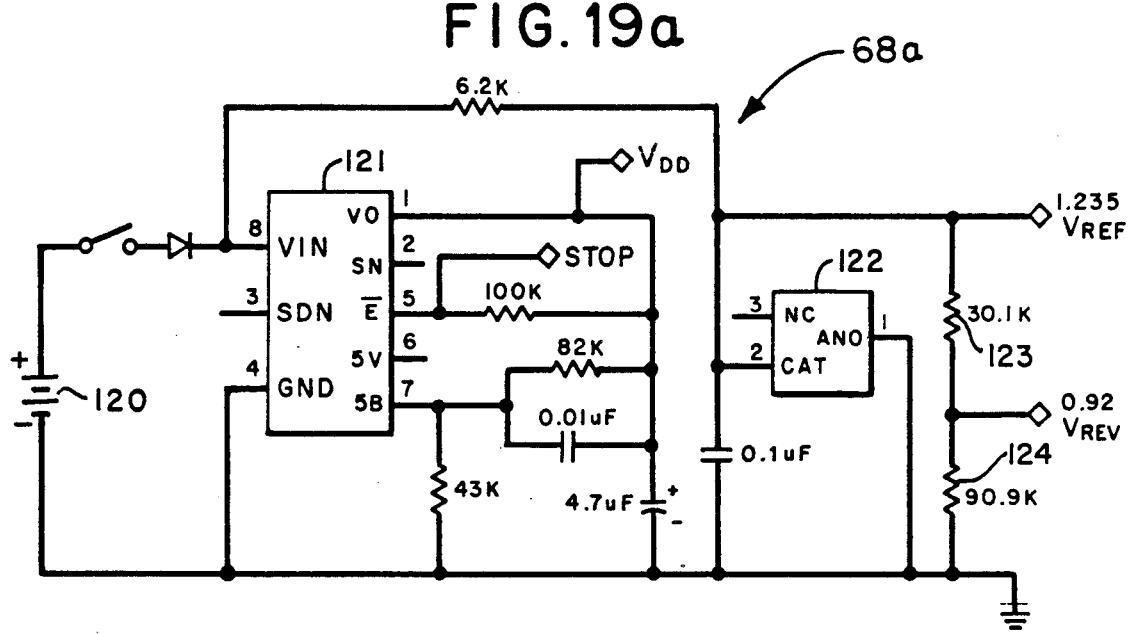

In the second preferred embodiment, also advantageously adapted for use with the TDx ® and similar analyzers, the transducer circuit means 65 of FIGS. 15 and 15a is replaced with an alternative transducer circuit means 65a which is illustrated in FIGS. 19 and 19a. Also, as illustrated in FIGS. 16b 16c, 17a. and 18a the electrically conductive socket means 150 of the first embodiment is replaced by a T-shaped, rigid printed wiring board 150a having electrically conductive sockets 142j–m connected by printed conductors 142n–q to rigid electrically conductive connector pins 151a–d. In this embodiment, the board 150a sits in the bottom of the chamber 138 with the sockets 142j–m positioned in openings 140a–d The pins 151a–d extend downwardly through opening 139 of the chamber 138 into the upper carousel 128 and are connected by conventional means to points of the transducer circuit 65a which is mounted on printed circuit board 165. In addition, in the second preferred embodiment, the LED 70a which comprises the optical output means is mounted on an insulating spacer 170a which is in turn mounted to the printed circuit board 165 so that the LED 70a preferably extends through an opening in the top surface 128 of the carousel 125 adjacent to the eleventh sample opening. In this position, the LED 70a optimally interfaces with the photodetector of the standard optical code reader of the TDx ® analyzer. In other respects concerning the adaptation of the TDx ® carousel, the adaptor means 152, and the sensor unit 60, the first and second preferred embodiments are substantially identical.

In contrast to transducer circuit means 65, transducer circuit means 65a converts the voltage differential generated between the pins 14b–d of each ion selective electrode and the reference voltage on pin 14a to a digitally encoded optical signal which has a value indicative of the concentration of the electrolyte detected by the electrode. The optical signal is suitable for reading by the existing, conventional optical bar code reader of the TDx ® or similar instrument and its value may be processed using conventional linear interpolation techniques as described with respect to the first embodiment to determine the precise concentration of each electrolyte.

The transducer circuit means 65a includes input buffer means 72, offset adjust means 74, analog switch means 76, integrator means 82, and pulse circuit means 84 which correspond to the like-referenced elements of the transducer circuit means 65. However, in transducer circuit means 65a, the offset adjust means includes 1M ohm potentiometers in lace of the 200 K ohm potentiometers used in the transducer circuit means 65. In addition the 1.02 V voltage reference applied to the first B input terminal of the analog switch means 76 in transducer circuit means 65 is replaced with a current reference comprised of a 1.235 reference voltage in series with a 294 K ohm resistor in transducer circuit means 65a. Also the integrator means 82 in transducer circuit means 65a employs a 330 pF feedback capacitor, a 100 K ohm input resistor, and a 47 K ohm pull-down resistor instead of the 1000 pF feedback capacitor, 48.7 K ohm input resistor, and 75 K ohm pull-down resistor used in transducer circuit means 65. Also in transducer circuit means 65a, the pulse circuit means 84 has its reset terminal LRST connected to receive a COUNT signal, which is described in detail below, instead of to the battery voltage VBATT as in transducer circuit means 65. Also, the threshold THRESH and discharge DISH terminals of the pulse circuit means 84 are connected to the junction of a 16.5 K ohm resistor and 1000 pF capacitor in transducer circuit means 65a whereas in transducer circuit means 65 a 75 K ohm resistor is used instead. It will be apparent to persons skilled in the art that while the identified variations constitute the best way presently known of constructing the transducer circuit means 65a of the second preferred embodiment, they do not substantially alter the basic operation of the input buffer means 72, offset adjust means 74, analog switch means 76, integrator means 82, or pulse circuit means 84 described above with respect to the transducer circuit means 65 of the first preferred embodiment.

In transducer circuit means 65a, the pulses output by the pulse circuit means 84 are input to one terminal of a NAND gate 79. The other input terminal of the NAND gate 79 receives a STOP signal from the preferred power supply means 68a of the transducer circuit means which iu illustrated in FIG. 19a and described in detail below. The power supply means 68a generates a low STOP signal when the DC voltage produced by a battery power source drops below a predetermined level. The low STOP signal clamps the output of the NAND gate 79 high which forward biases the diode 96a and prevents the feedback capacitor of the integrator means 82 from discharging. Consequently the integrator means 82 is prevented from triggering the pulse circuit means 84 and the transducer circuit means 65a is consequently disabled from energizing the optical output means 70a to transmit electrolyte concentration data to the TDx ® or other instrument. This no-data state thus provides a "low battery" indication to the instrument.

The pulses output by the pulse circuit means 84 are also input as clock signals to a counter means 99 which is comprised of a 12-bit counter 99a and two D flip-flops 99b and 99c configured as a 2-bit counter. The 12-bit counter 99a is preferably a 74HC4040 counter or equivalent and the D flip-flops are preferably 74HC4013 flip-flops or equivalents. The counter means 99 counts the pulses generated by the pulse circuit means 84 over a predetermined time interval and outputs a digital signal comprising a 14-bit count value.

The 14-bit count value is input in parallel to a 16-bit data selector means 112 comprised of two cascaded 8-bit data selectors 112a and 112b. Data selectors 112a and 112b are preferably 74HC4512B data selectors or equivalents. Data selector 112a receives the 7 least significant bits of the count value on inputs D0–D6 with the least significant of this group of bits corresponding to input D6 and the most significant to input D0. Input D7 of the data selector 112a receives a SYNC or channel indicator bit. Data selector 112b receives the 7 most significant count value bits on inputs D1–D7 with the most significant bit of this group corresponding to input D1 and the least significant bit to input D7. Input D0 is connected to the regulated battery voltage Vdd generated by the power supply means 68a and constitutes a start bit.

The start, count, and SYNC bits applied to the data selectors 112a and 112b are individually selected by the combination of bits applied to the select inputs A, B, and C of the data selectors 112a and 112b. The selected bit is switched to the output SEL of its corresponding data selector 112a or 112b. As will become apparent, the data selector means 112 comprises means for converting the 14-bit count value generated by the counter means 99 to a bit-serial, digitally-encoded signal.

The outputs SEL of the data selectors 112a and 112b are connected in parallel to an optical output means 50 comprised of a 300 ohm current-limiting resistor and series LED 70a. When the selected start, count, or SYNC bit is high, the LED 70a is energized. When the selected start, count, or SYNC bit is low, the LED 70a is not energized. The optical output means thus responds to the bit-serial digitally-encoded signal generated by the data selector means 112 to generate a corresponding digitally-encoded optical signal which provides an optical indication of the concentration of a preselected electrolyte in a sample under test. Because the optical signal is digitally-encoded, it is well adapted for reading and processing by the existing conventional optical code reader apparatus of the TDx ® or similar instruments.

In the preferred embodiment, the LED 70a is preferably an infrared LED such as an OP 297-B or equivalent. An infrared LED is preferred to maximize coupling with the photodetector of the TDx ® optical code reader. It is understood that different types of LED's may be found more suitable with various other instruments having different optical code readers.

Bit selection and timing signals are generated in the transducer circuit means 65a by timing means preferably comprising a 2.4576 MHz oscillator 114 and counters 115 and 117. Together the oscillator 114 and counters 115 and 117 perform the same function as the counter means 78 of the first preferred embodiment but with higher resolution and accuracy. The oscillator 114 is preferably an HC-18 cased, "AT" cut crystal oscillator and the counters 115 and 117 are preferably 74HC4060 and 74HC4020 counters respectively. The counters 115 and 117 divide down the 2.4576 MHz signal generated by the oscillator 114 to provide channel selection signals Q13 and Q14, a data selector select signal Q9 also designated as CL16, and bit selection signals Q6, Q7, and Q8 at the output of counter 117. Also generated is a count enable signal COUNT which is the logical NAND of the Q11 and Q12 signals output by counter 117 and the SYNC bit which is the logical NAND of the Q13 and Q14 channel selection signals.

The channel selection signals Q13 and Q14 are input to the S0 and S1 channel selection inputs of the analog switch means 76 and sequentially select each of channels 0–3. As previously described channel 0 is connected to the 0.92 V DC reference voltage generated by the power supply means 68a. Channels 1–3 are connected to the outputs of the input buffers 72 corresponding to pins 14b–d of the ion selective electrode means 10 which provide voltages corresponding to the concentration of preselected electrolytes in the sample under test. The oscillator division ratio provided by the counters 115 and 117 is selected to provide a desired dwell time for each selected channel. In the preferred embodiment, the division ratio is selected to provide a dwell time of approximately 0.853 seconds for each channel selection combination of Q13 and Q14. Thus, in the preferred embodiment, each channel 0–3 is sequentially selected for a period of 0.853 seconds.

The dwell time for each channel is preferably further divided into a desired counting period and a count transmit period In the preferred embodiment, the counting period is selected to comprise three-fourths of the dwell time or 0.64 seconds, and the count transmit period to comprise the remaining dwell time or 0.213 seconds. During the counting period the COUNT signal is low. In this state, the COUNT signal enables the pulse circuit means 84 to generate output pulses having duty cycle and rate related to the voltage on the channel selected by signals Q13 and Q14 and enables the pulse counter means 99 to count the pulses generated by the pulse circuit means and to generate the previously described 14-bit count value. Also in this state, the COUNT signal, which is input to the inhibit INH inputs of the data selectors 112a and 112b, prevents the data selector means 112 from outputting bits to the optical output means.

When the counting period comes to an end, the COUNT signal goes high and stays high for the remainder of the dwell period, i.e., the count transmit period. In this state, the COUNT signal disables the pulse circuit means 84 and pulse counter means 99 from generating or counting any further pulses. It also enables the data selectors 112a and 112b to receive the bit selection signals Q6–Q8 and the data selector select signal CL16 from the counter 117 to output selected start, count and SYNC bits to the LED 70a. During this period, the counter 117 counts through all eight bit selection combinations of Q6–Q8 four times. The first and third times, the data selector select signal CL16 is low and data selector 112b is selected The second and fourth times, the data selector select signal CL16 is high and data selector 112a is selected. The start, count, and SYNC bits for the selected channel are thus output sequentially to the LED 70a twice during the count transmit period in the order of start bit, count bits from most to least significant value, and SYNC bit.

The data transmission rate preferred for use with the TDx ® instrument is approximately 150 baud. However, persons skilled in the art will realize that higher or lower rates :an be obtained as desired by varying the frequency of the oscillator 114 and/or the division ratio of the counters 115 and 117.

At the end of the count transmit period, the combination of channel selection signals Q13 and Q14 changes to select the next sequential channel. The foregoing counting and transmitting operation is then repeated for the newly selected channel. At the end of the count transmit period when Q13 and Q14 are both high and channel 3 is selected, the counter 117 rolls over and selects channel 0. In this manner, the transducer circuit means 65a continuously cycles, selecting each channel sequentially, counting pulses related to the voltage of the selected channel and generating a count value related to the concentration of the electrolyte in the sample corresponding to the selected channel, converting the count value to a digitally-encoded, bit-serial signal, and transmitting the signal as digitally-encoded optical signals for detection by the optical code reader apparatus of a diagnostic instrument.

In the preferred embodiment, the SYNC signal is the logical NAND of channel selection signals Q13 and Q14. SYNC is generated by NAND gate 105a, which performs the same function as the synchronization circuit means 105 of the first preferred embodiment. The SYNC signal is maintained high when channels 0–2 are selected and goes low when channel 3 is selected in order to provide a synchronization or channel indication signal for use by a TDx ® or similar instrument.

In addition to the differences between the transducer circuit means 65 and transducer circuit means 65a which should already be apparent to those skilled in the art from the foregoing description, the operation of the transducer circuit means 65a also differs from the operation of the transducer circuit means 65 when the reference channel 0 is selected. In the transducer circuit means 65a, when the reference channel 0 is selected the current reference formed by the 1.235 V reference voltage and series 294 K ohm resistor connected to the channel 0–B input of the analog switch means 76 is switched into the non-inverting input of the integrator means 82. The current reference value is selected to cause the integrator means 82 and pulse circuit means 84 to generate a selected number of pulses during the counting period of the channel 0 in order to generate a reference count value. The reference count value is transmitted with the count values for the ion selective electrode channels and is useful in correlating the electrolyte concentration data generated by one transducer circuit means with the electrolyte concentration data generated by others or in correlating the electrolyte concentration data generated by the same transducer circuit means at various times. In the preferred embodiment, the selected current reference value produces a reference count of approximately 2500–3500.

Referring to FIG. 19a, the details of the preferred power supply), means 68a of the transducer circuit means 65a are illustrated. The power supply means 68a includes a battery 120, voltage reference diode 122, and voltage divider comprised of resistors 123 and 124 which generate voltage references of 1.235 VDC and 0.92 VDC, and which correspond to the like-referenced elements of power supply means 68 shown in FIG. 15a. In addition, connected between the terminals of the battery 120 and the voltage reference diode 122 is a voltage regulator 121. The voltage regulator 121, which is preferably an LP2951 or equivalent voltage regulator, is preferably configured as illustrated in FIG. 19a to generate a regulated voltage output Vdd of approximately 3.6 VDC which provides operating power for the electrical components of transducer circuit means 65a. When battery voltage reaches a level at which the regulator 121 can no longer maintain the regulated voltage Vdd at the desired 3.6 VDC level, the STOP signal output by the regulator 121 goes low, thereby causing the transducer circuit means 68a to enter the previously described "no-data" state and provide an indication that the battery needs replacing.

In operation the second preferred embodiment may be used to determine the concentration of preselected electrolytes in unknown samples in exactly the same manner as previously described with respect to the first preferred embodiment by using known high and low concentration electrolyte calibrator samples to generate a scale and a linear interpolation process to determine the concentration of preselected electrolytes in the unknown sample. The primary difference between the two embodiments is that the second preferred embodiment generates digital code values related to the concentrations of the preselected electrolytes whereas the first preferred embodiment generates an-analog signal having value related to the electrolyte concentrations.

In the first and second preferred embodiments, both of which are preferred for use with the TDx ® analyzer, it !as been found that it can take 45 minutes to an hour &o prepare and test all samples on the TDx ® carousel. During this time, it has been found that evaporation of the samples can occur and produce erroneously high electrolyte concentration readings. In order to compensate for the evaporation, it is preferred to load at least one position of the carousel, for example position 20 as illustrated in FIG. 17, with a sodium solution having a mid-range concentration such a: the buffer solution which is used to prime and store the ion selective electrodes. It is not necessary that the solution have a high precision concentration. Both prior to and after testing the other samples on the carousel, the concentration of the sodium solution is tested and recorded. The rate of change of the tested sodium concentration with time due to evaporation can be assumed to be linear and to correspond directly to the change in electrolyte concentration found for the other samples over time due to evaporation. Thus, by recording the starting and ending times of the test and the time each sample is tested, the slope of the change in concentration of the sodium solution can te used to correct the concentration found for each sample for evaporation.

FIGS. 20–23 illustrate a third and equally preferred embodiment of the electrolyte measuring apparatus of the invention. The third preferred embodiment generally comprises, similarly to the first and second preferred embodiments, ion selective electrode means 200 for generating a plurality of voltage differentials corresponding to the concentrations of a corresponding plurality of pre-selected electrolyte concentrations in a simple, transducer circuit means 210 for converting the voltage differentials to electrical signals having parameters related to the magnitudes of the voltage differentials, and optical output means 220 responsive to the electrical signals to generate optical signals having parameters related to the parameters of the electrical signals and representative of the concentrations of the pre-selected electrolytes in the sample. In the third preferred embodiment, like the first and second preferred embodiments, the ion selective electrode 200 is preferably constructed according to the teaching of the co-pending application previously identified and incorporated by reference herein. In contrast to the first preferred embodiment, in the third preferred embodiment the magnitudes of the electrical signals and the optical densities of the output optical signals relate to and are representative of the concentrations of the selected electrolytes in the sample rather than the duty cycles and the intensities of the signals. In the third preferred embodiment the optical output means 220 is operative in response to the electrical signals to selectively absorb light from an optical source 225 in order to generate optical signals readable by an optical detector 230 such as a PMT, rather than to generate optical light signals directly as in the first and second preferred embodiments.

Figure 20:
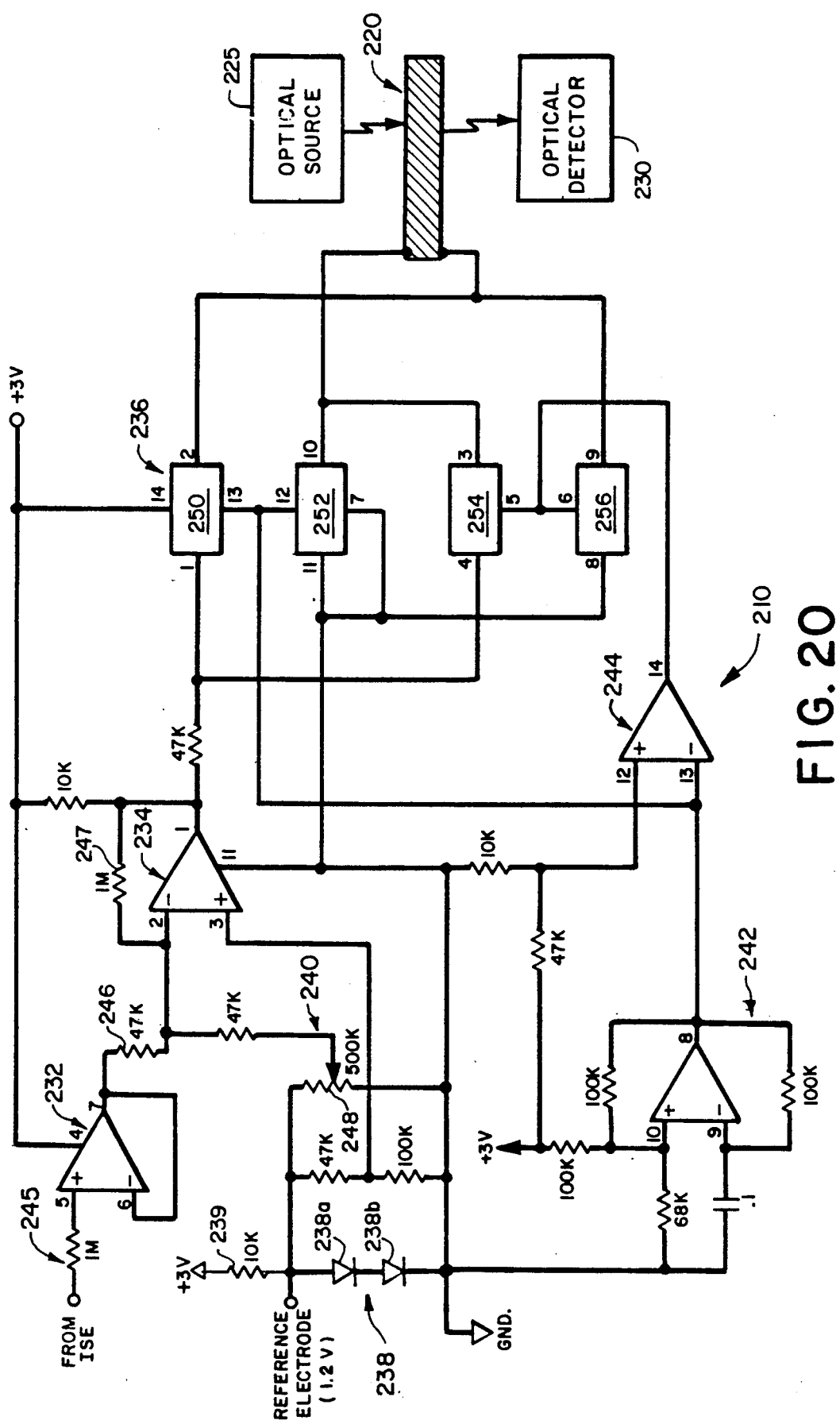
FIG. 20 is an electrical schematic diagram illustrating the details of an optical output means and a transducer circuit for converting voltage potentials on the ion selective electrodes to optical output signals comprising a portion of a third preferred embodiment of the electrolyte measuring apparatus of the invention.

Referring to FIG. 20, an electrical schematic diagram illustrating the details of the transducer circuit means 210 and optical output means 220 is shown. For convenience, the transducer circuit means 210 is illustrated as receiving only one input from the ion selective electrode 200. It is understood, however, that the transducer circuit means 210 is operative to sequentially process a plurality of voltage differentials generated by the ion selective electrode 200 by multiplexing the voltages in the same manner as described with respect to the first and second preferred embodiments. The transducer circuit means 210 generally comprises high impedance input buffer means 232, linear amplifier means 234, bilateral switch means 236, voltage reference means 238, offset adjustment means 240, oscillator means 242, and inverting driver means 244. The input buffer means 232 is suitably comprised of an operational amplifier configured as a source follower as illustrated having its non-inverting terminal connected to the ion selective electrode 200 to receive a voltage differential generated thereby through a 1 Mohm resistor 245. The input buffer means 232 provides high impedance isolation between the ion selective electrode 200 and the transducer circuit means 210 to prevent the flow of current through the detection sites of the ion selective electrode 200.

The output of the input buffer means 232 is connected to an input of the linear amplifier means 234. The linear amplifier means 234 is preferably comprised of an operational amplifier having its inverting terminal connected to the output of input buffer means 232 by a resistor 246 The gain of the linear amplifier 234 is determined by the values of the resistor 246 and a feedback resistor 247, the values of which are preferably selected to maintain the response of the transducer circuit means 210 within the linear operating range of the optical output means 220, which is described in detail below. The values illustrated for resistors 246 and 247 have been found to provide adequate linearity with the preferred ion selective electrode 200 and optical output means 220 which are described in detail below.

Also connected to the inverting terminal of the operational amplifier 234 is the output of the offset adjustment means 240, which includes a variable resistor 248. Similarly to the offset adjustment means of the first and second preferred embodiments, the offset adjustment means 240 provides a variable voltage at the inverting terminal of the linear amplifier 234 to adjust the response of the amplifier 234 for a range of ion selective electrode output signal levels. The variable resistor 248 of the offset adjustment means 240 is preferably adjusted to maintain the response of the linear amplifier 134 within the linear operating range of the optical output means 220. As described above with respect to the first preferred embodiment, the variable resistor 248 of the offset adjustment means 240 may be replaced by fixed resistor values if an ion selective electrode 200 having known output signal levels is employed.

The output of the linear amplifier 234 is connected in parallel to two inputs of the bilateral switch means 236. The bilateral switch means 236 preferably comprises four parallel solid state switches 250, 252, 254, and 256. The switches are preferably packaged in a single integrated circuit part No. HEF4066 or equivalent. The switches are preferably controlled in pairs with switches 250 and 252 comprising one pair and switches 254 and 256 comprising a second pair. The inputs of one switch from each pair, i.e., switches 250 and 254, are connected in parallel to the output of the linear amplifier means 234. The inputs of the remaining switch from each pair, i.e., switches 252 and 256, are connected to ground. The outputs of the switches 250 and 256 are connected in parallel to one terminal of the optical output means 220 and the outputs of the switches 252 and 254 are connected in parallel to a second terminal of the optical output means 220. The control terminals of the first pair of switches 250 and 252 are connected to the signal input of the inverting driver 244 and the control terminals of the second pair of switches 254 and 256 are connected to the output of the inverting driver 244 so that only one pair of switches is actuated at any time.

The optical output means 220 is preferably a liquid crystal light valve of the type known to those skilled in the art. A suitable light valve having desirable high impedance, low voltage, and large linear dynamic range characteristics is available from UCE, Inc. of Norwalk, Conn. In the second preferred embodiment, the selected light valve preferably has a transparent to opaque range in excess of three optical density units. The liquid crystal light valve is preferably driven by an AC source, preferably a square wave, to prevent the tendency of the light valve to drift back to its quiescent transparent condition after a short time when a DC drive signal is utilized.

The oscillator means 242 preferably comprises an operational amplifier feedback oscillator configured as illustrated to provide a 60 Hz. square wave signal. The output of the oscillator 242 is connected to the signal input of the inverting driver 244, which is preferably an operational amplifier configured as illustrated, and to the control terminals of the first pair of bilateral switches 250 and 252. The operational amplifiers of the oscillator 242, driver 244, input buffer means 232, and linear amplifier 234 are preferably provided in a single integrated circuit package, part no. TLC25L4 or an equivalent. The oscillator 242 and inverting driver 244 alternately actuate the first and second pairs of bilateral switches at a rate of 60 Hz. to drive the liquid crystal light valve 220 with alternating polarities of the electrical signal appearing at the output of the linear amplifier 234. The response time of the preferred liquid crystal light valve is such that it cannot respond to the alternating polarity of the drive signal at the 60 Hz. rate, but rather maintains a substantially fixed degree of opaqueness which is linearly related to the absolute magnitude of the alternating polarity drive signal.

The transducer circuit means 210 of the third preferred embodiment is suitably supplied by a single cell lithium battery having an output voltage of approximately +3 volts. The transducer circuit means 210 of the third preferred embodiment generates a reference voltage of approximately 1.2 volts from the supply voltage and applies the reference voltage to the reference electrode of the ion selective electrode 200. In the third preferred embodiment the voltage reference means 230 comprises a pair of series diodes 238a and 238b which are connected in series between the supply voltage and ground in series with a 10 K ohm current limiting resistor 239. The reference voltage is taken between the cathode of the first diode 238a and ground.

The third preferred embodiment is particularly advantageously employed in conjunction with existing automated centrifugal assay instruments of the type employing a multi-chamber test pack and conventional optical source and detector apparatus. An exemplary instrument of this type is the Vision ® automated centrifugal assay instrument manufactured and sold by Abbott Laboratories of North Chicago, Ill. The interfacing and utilization of the third preferred embodiment with the Vision ® instrument will now be described, it being understood that the Vision ® instrument is merely illustrative and that the third preferred embodiment is also advantageously employed in conjunction with other automated assay instruments having the general characteristics identified as well as with non-automated, stand-alone optical measuring apparatus.

Figure 21:
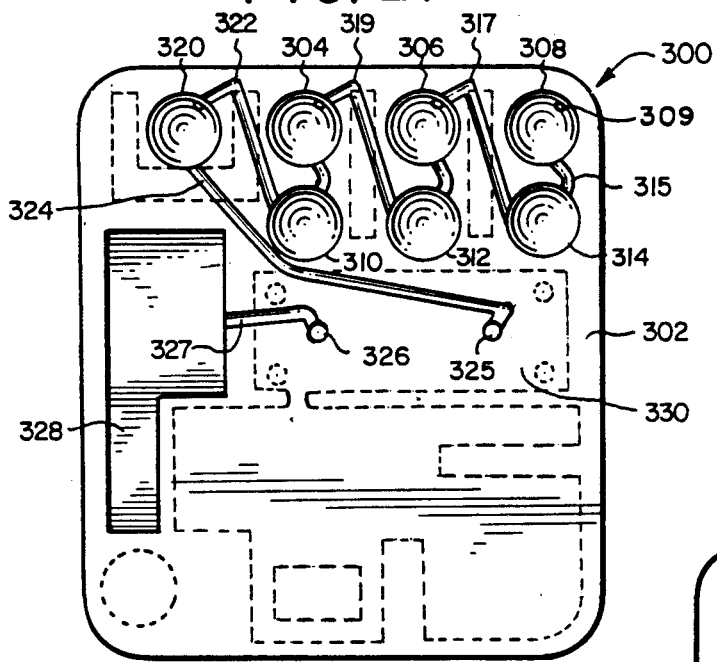
FIG. 21 is a plan view of the sample side of a centrifugal test cartridge of the type used with a conventional automated centrifugal assay instrument and which is adapted for use with a third preferred embodiment of the invention.
Figure 22:
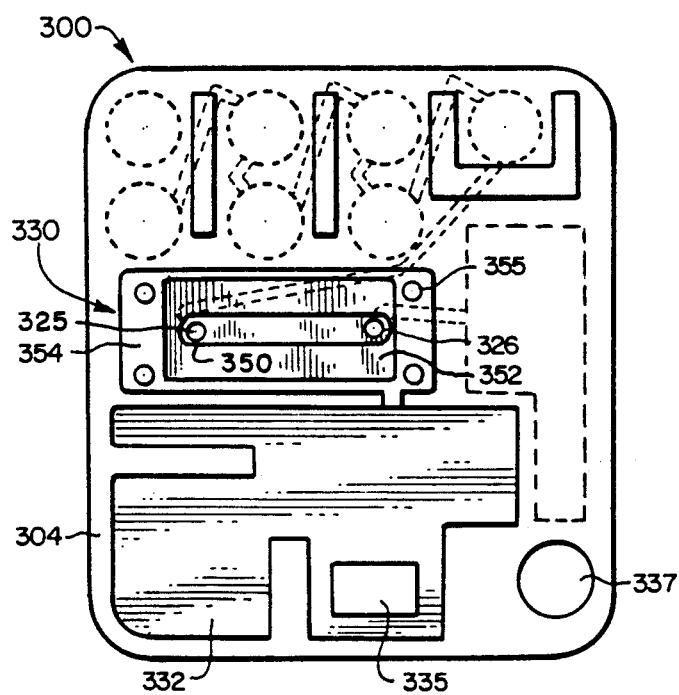
FIG. 22 is a plan view of the electronics side of the test cartridge illustrated in FIG. 21.

Referring to FIGS. 21 and 22, a multi-chamber test pack 300 of the type typically employed in the Vision ® instrument and which has been adapted for use with the third preferred embodiment of the invention is illustrated. The test pack 300 has a sample side 302 and an electronics side 304 which are separated by a solid wall (not shown). On the sample side 302, sample chambers 304, 306 and 308 are provided for receiving and holding a first known calibration sample, unknown sample to be tested, and a second known calibration sample respectively. Each of the sample chambers 304, 306, and 308 has a small sample insertion opening 309 into which a volume of sample may be introduced by syringe or other conventional means. After a sample has been introduced therein, the openings 309 may be closed by adhesive tape or other similar means to prevent escape. Holding chambers 310, 312 and 314 corresponding to sample chambers 304, 306 and 308 respectively are also formed on the sample side of the test cartridge 300. Each sample chamber and corresponding holding chamber is connected by a narrow fluid passageway 315. In addition, holding chambers 312 and 314 are connected to adjacent sample chambers 304 and 306 respectively by narrow fluid passages 317 and 319 respectively. Holding chamber 310 is connected to a delivery chamber 320 by a narrow fluid passageway 322. The delivery chamber 320 is connected by a narrow fluid passageway 324 to an opening 325 which extends through the solid wall of the test cartridge 300 separating the sample 302 and electronics 304 sides into an electrode mounting well 330, which is described in detail below. The opening 325 is preferably located near a first longitudinal end of the electrode mounting well 330. A second opening 326 extends through the solid wall into the electrode mounting well 330 near the opposite longitudinal end thereof and is connected by a narrow fluid passageway 327 to a waste chamber 328 formed in the sample side of the test cartridge.

Referring to FIG. 22, the electronic side 304 of the test cartridge 300 has an electronics compartment 332 formed therein. The electronic components comprising the preferred transducer circuit means 210 of the second preferred embodiment are mounted in the electronics compartment 332 and are preferably sealed by an epoxy or other fluid-tight sealant. In its most preferred form, the transducer circuit means 210 is embodied in a single hybrid integrated circuit chip. Alternatively, sufficient space is provided in the compartment 332 to accommodate a discrete embodiment of the transducer circuit means 210 as well. A window 335 comprising an opening in the surface of the electronic side 304 of the test cartridge 300 is formed immediately above the mounting location of the liquid crystal light valve which comprises the optical output means 220 of the preferred embodiment. In its most preferred form, the liquid crystal light valve 220 and the window 335 have a corresponding dimension of approximately ⅜ inch square. Alternatively, multiple windows and light valves could be provided in the cartridge 300 to allow multiple electrolyte measurements to be made simultaneously. In this case, the preferred transducer circuit means 210 would be duplicated for each light valve and the circuits would receive their inputs from the conductive areas of the electrode 200 in parallel. An alignment opening 337 is also preferably formed in the test cartridge 300 to facilitate mounting of the cartridge in the Vision ® instrument with the proper orientation.

Figure 23:
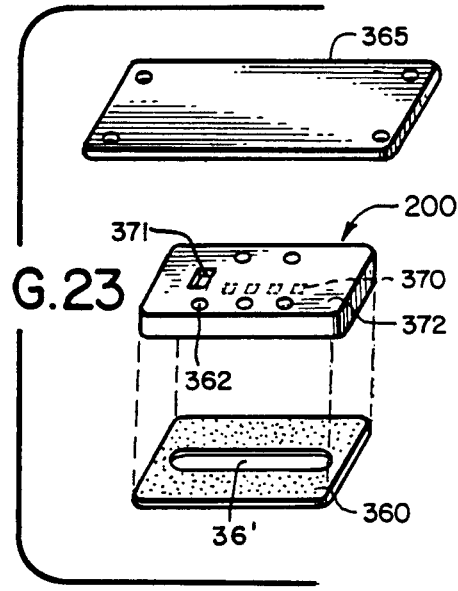
FIG. 23 is an exploded perspective view of an ion selective electrode, electrode mounting gasket, and electrode cover adapted to be mounted to the test cartridge illustrated in FIGS. 20 and 21.

Referring to FIGS. 22 and 23, the electrode mounting well 330 comprises an elliptical well portion 350 which extends longitudinally to encompass an area including both openings 325 and 326 from the sample side 302 of the test cartridge 300. The elliptical well portion 350 forms a sunken channel in a substantially rectangular counter-sunk electrode-receiving area 352 of the electrode mounting well 330. The electrode receiving area 352 is formed in a cover receiving area 354 which is slightly indented from the surface of the electronic side 304 of the test cartridge 300. The cover receiving area 354 has screw receiving openings formed therein in proximity to the four corners thereof. A gasket 360 preferably constructed of a silicon rubber or similar material suitable for forming a fluid-tight connection with the ion selective electrode 200 is formed in the shape of the electrode receiving area 352 and has an elliptical opening 361 formed therein corresponding to the elliptical channel 350. The gasket 360 is mounted flat in the electrode receiving area 352. The ion selective electrode 200, having a selected plurality of ion selective detection sites 370 and a reference electrode 371 on a first surface 372 thereof is mounted with the detection sites 370 and the reference electrode 371 facing downwardly atop the gasket 360 so that the detection sites 370 and the reference electrode 371 are aligned in the elliptical opening 361 of the gasket. The cover 365 is mounted in the cover receiving area 354 so that the top surface of the cover 365 is flush with the surface of the test cartridge 300. The cover 365 is preferably secured in place by screws (not shown) or other conventional fastening means. Alternatively, the cover 365 may be ultrasonically welded or otherwise permanently connected in place. The gasket 360 and the first surface 372 of the ion selective electrode 200 mate to form an elliptical fluid-tight channel about the detection sites 370 and reference electrode 371 in the channel 350. A plurality of flat conductive areas 362 on the ion selective electrode 200, which correspond to the conductive pins 14a–d of the electrode 10 of the first and second preferred embodiments, are conductively connected with each of the detection sites 370 and the reference electrode 371 in the same manner as the conductive pins in the first preferred embodiment. The conductive areas 362 are preferably connected to inputs of the transducer circuit means 210 by conventional light gauge electrical wire (not shown).

Figure 24:
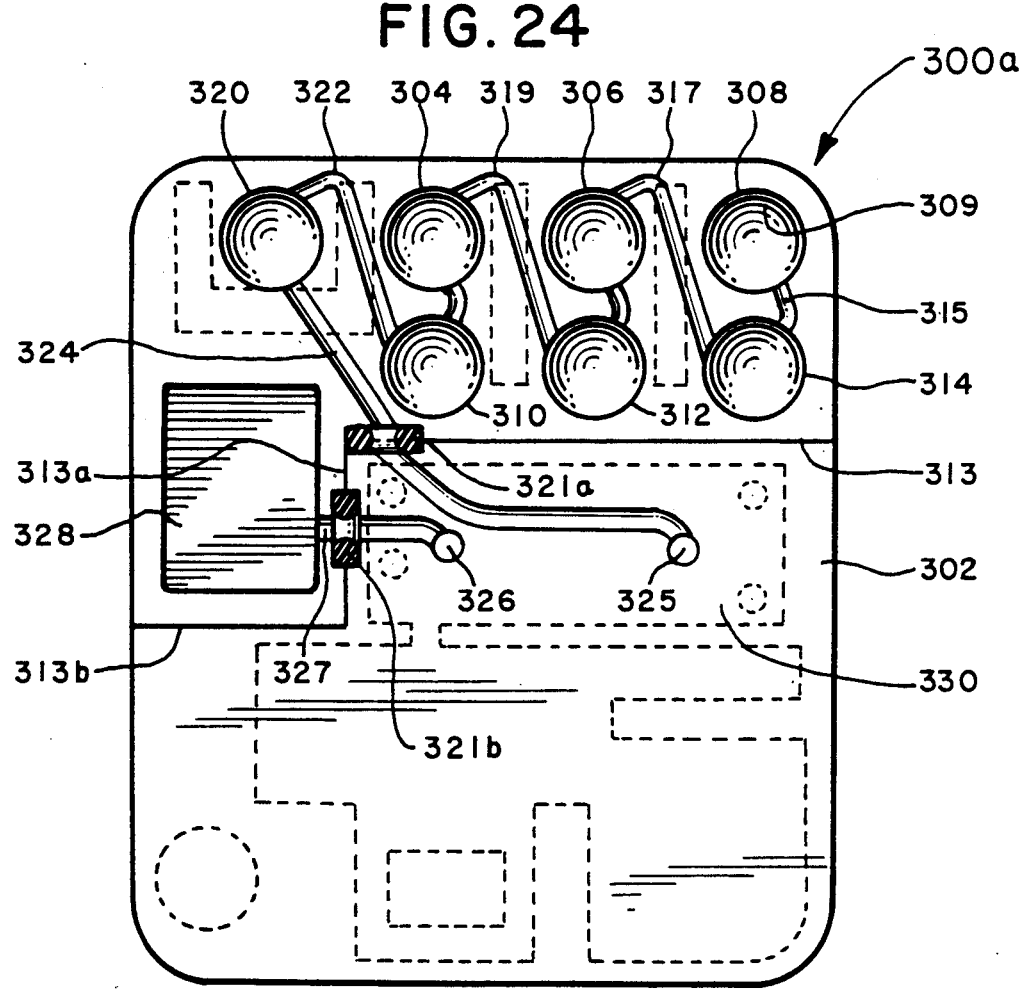
FIG. 24 is a plan view of the sample side of an alternative centrifugal test cartridge which is adapted for use with a third preferred embodiment of the invention.

An alternative embodiment to the one piece test cartridge 300 is illustrated in FIG. 24. In the alternative embodiment the cartridge 300a has separate sample and electronics sections. In this embodiment, the first section of the cartridge 300a containing the sample and waste chambers is disposable and the second section containing the electronics is reusable. The two sections are advantageously divided along a horizontal line 313 extending from the edge of the cartridge 300a between the chambers 310, 312, 314 and the electrode mounting well 330' along a vertical line 313a between the electrode mounting well 330 and the waste chamber 328, and along a horizontal line 313b extending to the edge of the cartridge 300a below the waste chamber 328. The two sections are preferably connected by a slide mount or other suitable means. In the advantageous application of the third preferred embodiment in centrifugal assay apparatus, which is described in detail below, the centrifugal force applied to the two sections may typically be in the range of 500 g's and assists in maintaining the two sections in fluid-tight connection. "O"-rings 321a, 321b and/or a sticky adhesive such as beeswax and rosin, paraffin, or a piezoelastic are provided to seal the separate sections at the fluid passageways 324 and 327. Additionally, connecting means such as locking tabs or the like (not shown) may also be provided if desired or if necessary for non-centrifugal applications.

Operation of the third preferred embodiment will now be described with reference to its particularly advantageous utilization in conjunction with the exemplary Vision ® centrifugal assay instrument described previously. In a preferred mode of operation, a first calibrator sample having a known, relatively low level concentration of one or more selected electrolytes of interest is introduced into the sample chamber 304 by suitable means such as a syringe. A second calibrator sample having a known relatively high concentration of the same electrolytes is introduced by suitable means into the sample chamber 308. The sample having unknown concentrations of the electrolytes of interest to be measured is introduced into the sample chamber 306. The test pack 300 is mounted in a test pack holder in the centrifuge of the assay instrument and is rotated at a high rate of speed, typically on the order of 1800 rpm's. The entire test pack 300 is then rotated by 90° which causes the calibrator samples and the unknown sample to be conducted from the respective sample wells 304, 306, and 308 to the corresponding holding chambers 310, 312, and 314 respectively. The test pack 300 is then rotated back to its original position, which causes the second calibrator sample to be conducted to the sample chamber 306, the unknown sample to be conducted to the sample chamber 304, and the first calibrator sample to be conducted to the delivery chamber 320. Next, the test cartridge 300 is again rotated by 90° which causes the unknown sample to be conducted to the holding chamber 310, the second calibrator sample to be conducted to the holding chamber 312, and the first calibrator sample to be conducted from the delivery chamber 320 into the fluid tight elliptical channel 350 where it comes into fluid contact with the detection sites 370 and reference electrode 371 of the ion selective electrode 200. Excess sample is conducted by the fluid passageway 327 into the waste chamber 328. In order to ensure an accurate and repeatable measurement of the selected electrolytes for which each of the detection sites 370 has an affinity, the test cartridge 300 is held in the rotated position for a minimum of approximately 15 seconds, during which time the first calibrator sample remains in contact with the detection sites 370 and reference electrode 371.

As in the first and second preferred embodiments, each detection site 370 causes a voltage differential having a magnitude related to the concentration of the electrolyte for which the particular site has an affinity to be generated between the reference electrode and the conductive area corresponding to that site. Each voltage is coupled into the transducer circuit means 210 by the input buffer means 232, is level adjusted by the adjustment offset means 248, and is amplified by the linear amplifier 234. The magnitude of the electrical signal appearing at the output of the linear amplifier 234 is linearly related to the concentration of the selected electrolyte. The oscillator means 242 and the inverting driver means 244 alternately actuate the first and second pairs of bilateral switches 236 to apply the electrical signal and ground to the contacts of the liquid crystal light valve 220 with alternating polarity. The liquid crystal light valve 220 responds to the alternating polarity drive signal by becoming opaque to a degree which is linearly-related to the magnitude of the electrical signal at the output of the linear amplifier means 234, i.e. the optical density of the light valve is linearly related to the magnitude of the electrical signal. The optical source 225 of the assay instrument is positioned to illuminate the liquid crystal light valve 220 on one side. The liquid crystal light valve 220 absorbs a portion of the light generated by the optical source 225 which is linearly related to the magnitude of the alternating polarity drive signal. The optical signal generated on the opposite side of the light valve 220 has intensity linearly related to the magnitude of the drive signal and to the optical density of the light valve 220. The optical density of the light valve 220, as indicated by the generated optical signal represents the concentration of the selected electrolyte in the sample. The optical signal is detected by the optical detector apparatus 230 of the assay instrument.

Subsequently, the test pack 300 is rotated between its original position and the 90° position in order to sequentially conduct first the unknown sample and then the second known calibrator sample into the fluid-tight channel 350 and into fluid contact with the detection sites 370 and reference electrode 371 of the ion selective electrode 200 for measurement in the same manner as described above. The test pack 300 is preferably not rotated after the second calibrator sample is brought into fluid contact with the ion selective electrode 200 so that a level of fluid always covers the ion selective membranes to prevent air pocket formation or contamination.

Since the level of the input voltage differential is adjusted by the offset adjustment means 240, and the gain of the linear amplifier means 234 is adjusted by the resistors 246 and 247 so that the transducer circuit means 210 operates within the linear response range of the liquid crystal light valve 220, the concentrations of the electrolytes of interest in the unknown sample are easily determined by linear interpolation from the optical absorption or density values derived for the two known calibrator samples in the same manner as described above with respect to the first preferred embodiment. Thus, in the third preferred embodiment, in contrast to the first and second preferred embodiments, the optical absorption or densities represented by the optical signals corresponding to the first and second calibrator samples and the unknown sample are linearly interpolated to obtain the concentrations of the electrolytes in the sample rather than the integrated intensities or count values of the optical signals.

The utilization of the third preferred embodiment in conjunction with existing automated centrifugal assay instruments in the manner described above provides several advantages particular to centrifugal-type electrolyte measuring apparatus. For instance, the use of ion selective electrode means as an electrolyte sensor allows greatly reduced volumes of sample and calibrators to be used, thus reducing cost. The use of smaller volumes also facilitates the testing of infants from whom it had been difficult in the past to obtain sufficient volumes of sample for adequate testing. In addition, the ability to use smaller volumes facilitates and simplifies test cartridge design since surface effects of the sample and calibrator fluids are minimized and do not impair conduction of the fluids in the test cartridge as is the tendency with larger volumes. Another advantage of this embodiment is that it can be used to perform blood hemolysis.

What have been described are certain aspects of apparatus for measuring electrolyte concentrations in fluid biological samples which constitute presently preferred embodiments of the invention. It is understood that the foregoing description and accompanying illustrations are merely exemplary and are not to be taken as limiting the scope of the invention, which is defined solely by the appended claims and their equivalents. Various changes and modifications to the preferred embodiments will be apparent to those skilled in the art. For example, the preferred ion selective electrode means utilized in the preferred embodiments may be replaced by chemical field effect transistor means which generate current as an electrical component indicative of electrolyte concentration rather than voltage. Such changes and modification can be made without departing from the spirit and scope of the invention. Accordingly, it is intended that all such changes and modifications be covered by the appended claims and their equivalents.

We claim:

1. Apparatus for measuring the concentration of electrolytes in a fluid sample, wherein the components of said apparatus are housed in a single unit, said components comprising:

container means for containing a sample to be measured;

sensor means operative when in fluid contact with a sample to generate an electrical signal having magnitude related to the concentration of at least one preselected electrolyte in said sample;

transducer means in communication with said sensor means and responsive to said electrical signal for generating at least one second signal having a parameter related to said magnitude of said electrical signal;

optical means responsive to said at least one second signal for generating at least one optical signal corresponding to said second signal and representing the concentration of said at least one preselected electrolyte of said sample; and optical reading means operative te detect said optical signal and measure variations in said optical signal as indicative of the concentration of said at least one preselected electrolyte.

2. The apparatus defined in claim 1 wherein said sensor means includes ion selective electrode means operative to generate at least one analog voltage having magnitude related to the concentration of said at least one preselected electrolyte.

3. The apparatus defined in claim 1 wherein said sensor means includes chemical field effect transistor means operative to generate at least one analog current having magnitude related to the concentration of said at least one preselected electrolyte.

4. The apparatus defined iu claim 1 wherein said sensor means includes chemical field effect transistor means operative to generate at least one analog voltage having magnitude related to the concentration of said at least one preselected electrolyte.

5. The apparatus defined in claim 1 wherein said optical means includes:

optical source means for generating light; and
   light valve means responsive to said second signal for absorbing a portion of said light to generate optical signals having a parameter related to the concentration of said at least one preselected electrolyte in said sample.

6. The apparatus defined in claim 1 wherein said optical means comprises light emitting diode means having a selected output wavelength.

7. The apparatus defined in claim 1 wherein said transducer means includes means for converting said at least one electrical signal into a said at least one second signal having duty cycle related to the magnitude of said electrical signal.

8. The apparatus defined in claim 1 wherein said transducer means includes means for converting said at least one electrical signal into a said at least one second signal having frequency related to the magnitude of said electrical signal.

9. The apparatus defined in claim 1 wherein said transducer means includes means for converting said at least one electrical signal into a said at least one second signal having pulse width related to the magnitude of said electrical signal.

10. The apparatus defined in claim 1 wherein said transducer means includes means for converting said at least one electrical signal into a said at least one second signal comprising alternating polarity pulses having magnitude related to the magnitude of said electrical signal.

11. The apparatus defined in claim 1 wherein said sensor means includes a plurality of electrode means attached to a substrate, at least one of which is a common reference electrode and at least one of which is an electrolyte detection electrode including means having an affinity for a preselected electrolyte for generating a plurality of voltage differentials each having magnitude related to the concentration of a preselected electrolyte.

12. The apparatus defined in claim 11 wherein each of said plurality of electrodes except said reference electrode includes means having an affinity for a different preselected electrolyte.

13. The apparatus defined in claim 11 wherein said transducer means includes:
   means for sequentially selecting each said electrolyte detection electrode to sequentially generate a plurality of said second signals each having a parameter related to the magnitude of the voltage differential between said electrolyte detection electrode and said common reference electrode; and
   means responsive to said means for selecting to sequentially drive said optical means with each of said plurality of second signals to sequentially generate a plurality of optical signals each representing the concentration of a preselected electrolyte in said sample.

14. The apparatus defined in claim 11, including:
   vessel means for holding said sample;
   interface means connected to said vessel means for mounting said electrode means in fluid-tight communication with said vessel means; and
   means forming a fluid-tight area about said reference electrode when said electrode means is mounted to said interface means in a selected storage position and adapted to maintain fluid in contact with said reference electrode when in said storage position.

15. The apparatus defined in claim 1 wherein said optical reading means is in visual alignment with said optical means for directly intercepting the path of said optical signal.

16. The apparatus defined in claim 15 wherein said optical reading means includes a photomultiplier tube.

17. Apparatus for measuring the concentration of electrolytes in a fluid sample wherein the components of said apparatus are housed in a single unit, said components comprising:
   container means for containing a sample to be measured;
   sensor means mounted in fluid-tight connection with said container means and operative when in fluid contact with said sample to generate at least one electrical signal having magnitude related to the concentration of at least one preselected electrolyte in said sample;
   transducer means in communication with said sensor means and responsive to said electrical signal for generating at least one second signal having a parameter related to the magnitude of said electrical signal;
   optical means responsive to said at least one second signal for generating at least one optical signal corresponding to said second signal and representing the concentration of said at least one preselected electrolyte in said sample;
   optical detector means for reading said at least one optical signal; and
   mounting means adapted for use in an automated assay instrument for mounting said sensor means, container means, transducer means, and optical means.

18. The apparatus defined in claim 17 wherein said sensor means includes ion selective electrode means operative to generate at least one electrical voltage signal having magnitude related to the concentration of said at least one preselected electrolyte.

19. The apparatus defined in claim 17 wherein said sensor means includes chemical field effect transistor means operative to generate at least one electrical current signal having magnitude related to the concentration of said at least one preselected electrolyte.

20. The apparatus defined in claim 17 wherein said sensor means includes field effect transistor means operative to generate at least one electrical voltage signal having magnitude related to the concentration of said at least one preselected electrolyte.

21. The apparatus defined in claim 17 wherein said optical means includes light emitting diode means having a selected output wavelength.

22. The apparatus defined in claim 17 wherein said transducer means includes means for converting said at least one electrical signal into a said at least one second signal having duty cycle related to the magnitude of said electrical signal.

23. The apparatus defined in claim 17 wherein said transducer means includes means for converting said at least one electrical signal into a said at least one second signal having frequency related to the magnitude of said electrical signal.

24. The apparatus defined in claim 17 wherein said transducer means includes means for converting said at least one electrical signal into a said at least one second signal having pulse width related to the magnitude of said electrical signal.

25. The apparatus defined in claim 17 wherein said sensor means includes a plurality of electrodes, at least one of which is a common reference electrode and at least one of which is an electrolyte detection electrode including means having an affinity for a preselected electrolyte for generating at least one voltage differential having magnitude related to the concentration of a preselected electrolyte.

26. The apparatus defined in claim 25 wherein each of said plurality of electrodes except said reference electrode includes means having an affinity for a different preselected electrolyte.

27. The apparatus defined in claim 25 wherein said transducer means includes:
   means for sequentially selecting each said electrolyte detection electrode to sequentially generate a plurality of said second signals each having a parameter related to the magnitude of the voltage differential between said electrolyte detection electrode and said common reference electrode; and
   means responsive to said means for selecting to sequentially drive said optical means with each of said plurality of second signals to sequentially generate a plurality of optical signals each representing the concentration of a preselected electrolyte in said sample.

28. The apparatus defined in claim 25, including:
   vessel means for holding said sample;
   interface means connected to said vessel means for mounting said electrode means in fluid-tight communication with said vessel means; and
   means forming a fluid-tight area about said reference electrode when said electrode means is mounted to said interface means in a selected storage position and adapted to maintain fluid in contact with said reference electrode when in said storage position.

29. The apparatus defined in claim 17 wherein said container means comprises fluid vessel means for containing said sample and interface means connected to said fluid vessel means for removably mounting said electrode means in fluid communication with said vessel means.

30. The apparatus defined in claim 29 wherein said interface means comprises alignment means adapted to mate with a portion of said electrode means for aligning said electrode means with a selected orientation.

31. The apparatus defined in claim 29 wherein said vessel means include gasket means for engaging said substrate and forming a fluid-tight connection with said substrate about said electrode means when said electrode means is mounted to said interface means.

32. The apparatus defined in claim 17 wherein said mounting means comprises:
   adaptor means for mounting said container means and said electrode means as a single unit;
   rotatable carousel means having a plurality of sample mounting positions with at least one of said positions being adapted to mount said adaptor means;
   electrical mounting means mounted to said carousel means for mounting said transducer means and said optical means; and
   electrical connector means for electrically connecting said electrode means and said transducer means.

33. The apparatus defined in claim 32 wherein said container means includes key means and said adaptor means includes key receiving means for receiving the key means of selected container means to mount said selected container means with proper orientation.

34. The apparatus defined in claim 17 wherein said optical detector means is in visual alignment with said optical means for directly intercepting the path of said at least one optical signal.

35. Apparatus for use with centrifugal-type sample analyzer of the type having optical source means for providing a first optical signal and optical detector means for detecting a second optical signal form-measuring the concentration of electrolytes in a fluid sample, comprising:
   cartridge means adapted for use in measuring the concentrations of electrolytes in a fluid sample in a centrifugal apparatus;
   centrifugal head means capable of rotating about a first axis and adapted to removably hold said cartridge means;
   sample container means mounted in said cartridge means for containing a sample;
   sensor means mounted in said cartridge means in fluid-tight communication with said sample container means and operative when in fluid contact with said sample to generate at least one electrical signal having magnitude related to the concentration of at least one preselected electrolyte in said sample;
   transducer means mounted in said cartridge means in communication with said sensor means and responsive to said at least one electrical signal for generating at least one second signal having a parameter related to the magnitude of said at least one electrical signal; and
   optical means mounted in said cartridge means for intercepting the path of said first optical signal and being responsive to said at least one second signal for absorbing a portion of said first optical signal to generate at least one second optical signal having intensity related to the concentration of said at least one preselected electrolyte in said sample.

36. The apparatus defined in claim 35 wherein said sensor means comprises ion selective electrode means operative to generate at least one electrical voltage signal having magnitude related to the concentration of said at least one preselected electrolyte.

37. The apparatus defined in claim 35 wherein said sensor means includes chemical field effect transistor means operative to generate at least one electrical current signal having magnitude related to the concentration of said at least one preselected electrolyte.

38. The apparatus defined in claim 35 wherein said sensor means includes field effect transistor means operative to generate at least one electrical voltage signal having magnitude related to the concentration of said at least one preselected electrolyte.

39. The apparatus defined in claim 35 wherein said optical means comprises liquid crystal light valve means having crystal polarization responsive to said second signal for absorbing a portion of said first optical signal related to the value of said second signal to generate said at least one second optical signal having intensity related to the concentration of said at least one preselected electrolyte in said sample.

40. The apparatus defined in claim 35 wherein said sample container means includes:
   a plurality of sample chambers formed in said cartridge means in sequential fluid communication for containing a plurality of samples to be tested;
   a fluid-tight sensor mounting well for containing said sensor means;
   at least one of said sample chambers being in fluid communication with said mounting well; and
   a waste chamber in fluid communication with said mounting well;
   said chambers being arranged so that when said centrifugal head means is rotated about said axis and wherein said centrifugal head means further includes means to rotate said cartridge means about a second axis said plurality of samples are conducted sequentially into fluid contact with said sensor means.

41. The apparatus defined in claim 35 wherein said electrode means includes a plurality of electrodes, at least one of which is a common reference electrode and at least one of which is an electrolyte detection electrode including means having an affinity for a preselected electrolyte for generating at least one electrical voltage signal having magnitude related to the concentration of a preselected electrolyte in the sample.

42. The apparatus defined in claim 41 wherein each of said plurality of electrodes except said reference electrode includes means having an affinity for a different preselected electrolyte.

43. The apparatus defined in claim 35 wherein said transducer means includes means for converting said at least one electrical signal into at least one second signal comprising alternating polarity pulses each having magnitude related to the magnitude of said electrical signal.

44. The apparatus defined in claim 43 wherein said transducer means includes means for applying said alternating polarity pulses to drive said optical means.

45. Apparatus for measuring the concentration of electrolytes in a fluid sample, wherein the components of said apparatus are housed in a single unit, said components comprising:

container means for containing a fluid sample;

sensor means mounted in fluid communication with said container means and operative when in fluid contact with a sample to generate an analog signal having a parameter with value related to the concentration of a preselected electrolyte in said sample;

transducer means in communication with said sensor means for generating a digital signal having value related to the value of the parameter of said analog signal;

optical means responsive to said digital signal for generating an optical signal corresponding to said digital signal to provide an optical indication of the concentration of said preselected electrolyte in said sample: and optical reading means operative to detect and measure said optical signal as indicative of the concentration of said preselected electrolyte.

46. The apparatus defined in claim 45 wherein said sensor means includes ion selective electrode means operative to generate an analog voltage having magnitude related to the concentration of said preselected electrolyte.

47. The apparatus defined in claim 45 wherein said sensor means includes chemical field effect transistor means operative to generate an analog current having magnitude related to the concentration of said preselected electrolyte.

48. The apparatus defined in claim 45 wherein said sensor means includes chemical field effect transistor means operative to generate an analog voltage having magnitude related to the concentration of said preselected electrolyte.

49. The apparatus defined in claim 45 wherein said sensor means includes a plurality of sensor means each operative to generate an analog signal having a parameter with value related to the concentration of a preselected electrolyte in said sample;

wherein said transducer means includes means for sequentially selecting each of said sensor means to sequentially generate a plurality of said digital signals each having value related to the value of the parameter of the analog signal generated by the selected sensor means;

wherein said optical means is responsive to each of said plurality of digital signals to generate a corresponding plurality of optical signals; and wherein said optical reading means is responsive to each of said optical signals.

50. The apparatus defined in claim 45 including container means mounted in fluid communication with said sensor means for holding said sample in fluid contact with said sensor means.

51. The apparatus defined in claim 50 wherein said container means includes means for forming a fluid-tight seal with said sensor means.

52. The apparatus defined in claim 46 wherein said mounting means comprises:

adaptor means for mounting said container means and said electrode means as a single unit;

rotatable carousel means having a plurality of sample mounting positions with at least one of said positions being adapted to mount said adaptor means;

electrical mounting means mounted to said carousel means for mounting said transducer means and said optical means; and electrical connector means for electrically connecting said electrode means and said transducer means.

53. The apparatus defined in claim 45 wherein said transducer means includes:

pulse generator means responsive to said analog signal for generating a plurality of pulses; and counter means for counting said pulses to generate said digital signal comprising a count value related to the concentration of said preselected electrolyte in said sample.

54. The apparatus defined in claim 53 wherein said transducer means includes means for converting said digital signal to a bit-serial digitally-encoded pulse train for communication to said optical means.

55. The apparatus defined in claim 53 wherein said pulse generator means includes means responsive to said analog signal for generating a plurality of pulses with duty cycle related to said parameter of said analog signal.

56. The apparatus defined in claim 55 wherein said counter means includes means for counting said pulses over a predetermined time interval to generate said digital signal.

57. The apparatus defined in claim 45 wherein said optical reading means is in visual alignment with said optical means for directly intercepting the path of said optical signal.

58. Apparatus for measuring the concentration of an electrolyte in a fluid sample, wherein the components of said apparatus are housed in a single unit, said components comprising:

container means for containing a fluid sample;

sensor means mounted in fluid communication with said container means and operative when in fluid contact with said sample to generate an analog signal having a parameter with a value related to the concentration of a preselected electrolyte in said sample;

transducer means in communication with said sensor means for generating a first digital signal having a value related to the value of the parameter of said analog signal;

optical means responsive to said first digital signal for generating an optical signal corresponding to said first digital signal;

optical detector means responsive to said optical signal for generating a second digital signal corresponding to said first digital signal and providing an indication of the concentration of said preselected electrolyte in said sample; and means adapted for mounting in an automated assay instrument for mounting said container means sensor means, transducer means, and optical means.

59. The apparatus defined in claim 58 wherein said sensor means includes ion selective electrode means operative to generate an analog voltage having magnitude related to the concentration of said preselected electrolyte.

60. The apparatus defined in claim 58 wherein said sensor means includes chemical field effect transistor means operative to generate an analog current having magnitude related to the concentration of said preselected electrolyte.

61. The apparatus defined in claim 58 wherein said sensor means includes chemical field effect transistor means operative to generate an analog voltage having magnitude related to the concentration of said preselected electrolyte.

62. The apparatus defined in claim 58 wherein said sensor means includes a plurality of sensor means each operative to generate an analog signal having a parameter with value related to the concentration of a preselected electrolyte in said sample;

wherein said transducer means includes means for sequentially selecting each of said sensor means to sequentially generate a plurality of said first digital signals each having value related to the value of the parameter of the analog signal generated by the selected sensor means;

wherein said optical means is responsive to each of said plurality of first digital signals to generate a corresponding plurality of optical signals; and wherein said optical detector means is responsive to each of said optical signals to generate a plurality of second digital signals, each providing an indication of the concentration of a said preselected electrolyte in said sample.

63. The apparatus defined in claim 58 including container means mounted in fluid communication with said sensor means for holding said sample in fluid contact with said sensor means.

64. The apparatus defined in claim 63 wherein said container means includes means for forming a fluid-tight seal with said sensor means.

65. The apparatus defined in claim 58 wherein said transducer means includes:

pulse generator means responsive to said analog signal for generating a plurality of pulses; and counter means for counting said pulses to generate said digital signal comprising a digital count value related to the concentration of said preselected electrolyte in said sample.

66. The apparatus defined in claim 65 wherein said transducer means includes means for converting said digital signal to a bit-serial digitally-encoded pulse train for communication to said optical means.

67. The apparatus defined in claim 65 wherein said pulse generator means includes means responsive to said analog signal for generating a plurality of pulses with duty cycle related to said parameter of said analog signal.

68. The apparatus defined in claim 67 wherein said counter means includes means for counting said pulses over a predetermined time interval to generate said digital signal.

69. The apparatus defined in claim 58 wherein said optical detector means is in visual alignment with said optical means for directly intercepting the path of said optical signal.

* * * * *